(12) United States Patent
Takimiya et al.

(10) Patent No.: US 8,124,964 B2
(45) Date of Patent: Feb. 28, 2012

(54) FIELD-EFFECT TRANSISTOR

(75) Inventors: Kazuo Takimiya, Higashihiroshima (JP); Hideaki Ebata, Higashihiroshima (JP); Hirokazu Kuwabara, Tokyo (JP); Masaaki Ikeda, Tokyo (JP); Tatsuto Yui, Tokyo (JP)

(73) Assignees: Nippon Kayaku Kabushiki Kaisha, Tokyo (JP); Hiroshima University, Hiroshima (JP)

( * ) Notice: Subject to any disclaimer, the term of this patent is extended or adjusted under 35 U.S.C. 154(b) by 254 days.

(21) Appl. No.: 12/311,771

(22) PCT Filed: Oct. 19, 2007

(86) PCT No.: PCT/JP2007/070416
§ 371 (c)(1),
(2), (4) Date: Apr. 10, 2009

(87) PCT Pub. No.: WO2008/047896
PCT Pub. Date: Apr. 24, 2008

(65) Prior Publication Data
US 2010/0032655 A1 Feb. 11, 2010

(30) Foreign Application Priority Data

Oct. 20, 2006 (JP) .................................. 2006-285872
Mar. 9, 2007 (JP) .................................. 2007-060569

(51) Int. Cl.
*H01L 29/08* (2006.01)
(52) U.S. Cl. ...................... 257/40; 438/99; 257/E51.005
(58) Field of Classification Search .................... 257/40, 257/E51.005; 438/99
See application file for complete search history.

(56) References Cited

U.S. PATENT DOCUMENTS 7,368,331 B2 * 5/2008 Hirai .............................. 438/149
7,816,673 B2 * 10/2010 Park et al. ........................ 257/40

FOREIGN PATENT DOCUMENTS
EP 0 592 919 A1 4/1994
(Continued)

OTHER PUBLICATIONS
The International Search Report dated Jan. 22, 2008.
(Continued)

*Primary Examiner* — Trung Q Dang
(74) *Attorney, Agent, or Firm* — Nields, Lemack & Frame, LLC

(57) ABSTRACT

Disclosed is a field-effect transistor characterized by using a compound represented by the formula (1) below as a semiconductor material.

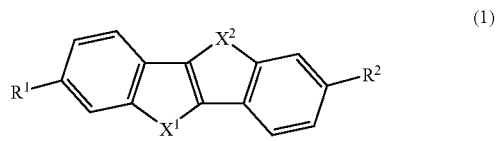

(1)

(In the formula (1), $X^1$ and $X^2$ independently represent a sulfur atom, a selenium atom or a tellurium atom; and $R^1$ and $R^2$ independently represent an unsubstituted or halogeno-substituted $C_1$-$C_{36}$ aliphatic hydrocarbon group.)

28 Claims, 3 Drawing Sheets

FOREIGN PATENT DOCUMENTS

| | | |
|---|---|---|
| EP | 1 847 544 A1 | 10/2007 |
| JP | 3-48686 | 3/1991 |
| JP | 6-192267 | 7/1994 |
| JP | 2001-515933 | 9/2001 |
| JP | 2005-281180 | 10/2005 |
| JP | 2005-322895 | 11/2005 |
| WO | 99/12989 A1 | 3/1999 |
| WO | 2006/077888 | 7/2006 |

OTHER PUBLICATIONS

J.Am.Chem.Soc. 2005, 127, 4986-4987; Marcia M. Payne et al.; "Organic Field-Effect Transistors from Solution-Deposited Functionalized acenes With Mobilities as High as 1cm/2/V.s".

J.Am.Chem. Soc. 2006, 128, p. 3044-3050; Kazuo Takimiya et al.; "2,7-Diphenyl[1]benzoselenopheno[3,2-b][1]benzoselenophene as a stable organic semiconductor for a high-performance field-effect transistor".

Liquid Crystals (2003), 30(5), p. 603-610; Bedrich Kosata et al.; "Novel liquid crystals based on [1]benzothieno[3,2-b][1]benzothiophene".

Collect, Czech, Chem. Commun, 67(5), p. 645-664, 2002; Bedrich Kosata et al.; "Reactivity of [1]benzothieno[3,2-b][1]benzothiophene-electrophilic and metallation reactions".

European Communication, dated Dec. 9, 2010, in corresponding foreign application EP 07 83 0150.4.

\* cited by examiner

A

B

C

D

E

FIELD-EFFECT TRANSISTOR

TECHNICAL FIELD

The present invention relates to a field-effect transistor. More specifically, the present invention relates to a field-effect transistor using a predetermined organic heterocyclic compound as a semiconductor material, and a method for manufacturing the same.

BACKGROUND ART

A field-effect transistor generally has a structure in which a source electrode and a drain electrode are formed on a semiconductor material on a substrate and a gate electrode, etc. is formed on these electrodes via an insulating layer, and is widely used not only in integrated circuits as a logic element but also in switching elements, etc. At present, inorganic semiconductor materials mostly formed of silicon are used in the field-effect transistors. Particularly, a thin-film transistor using amorphous silicon and formed on a substrate of e.g., glass is applied to displays, etc. When such an inorganic semiconductor material is used for manufacturing field-effect transistors, treatment must be performed at high temperature and in vacuum. Thus, a high investment is required for equipment and much energy is required for manufacturing, with the result that cost is extremely increased. In addition, these materials are exposed to high temperature during a field-effect transistor manufacturing process. Thus, a substrate such as a film or a plastic substrate having insufficient heat resistance cannot be used. The application field thereof is limited.

In contrast, research and development have been made on field-effect transistors using an organic semiconductor material requiring no high-temperature treatment during a field-effect transistor manufacturing process. Use of an organic material allows manufacturing in a low-temperature process and enlarges the range of materials that can be used as a substrate. As a result, it becomes possible to realize manufacturing of field-effect transistors more flexible, lighter and more irrefrangible than conventional ones. Also, it may be possible to manufacture a large-area field-effect transistor at low cost by further applying a solution containing an organic semiconductor material and employing a technique, e.g., printing such as inkjet printing, in the manufacturing step for a field-effect transistor.

However, most of the compounds conventionally used as an organic semiconductor material are insoluble or extremely less soluble in an organic solvent. Therefore, the aforementioned inexpensive techniques such as coating and inkjet printing cannot be used. A thin film is inevitably formed on a semiconductor substrate by a relatively expensive technique such as vacuum deposition. Materials (compound) suitable for practical printing were virtually not present. Even if a material soluble in an organic solvent, the semiconductor characteristics thereof are far from a practical level. Actually, there is only a material having low carrier mobility. Nevertheless, it is important to develop a semiconductor material which enables to manufacture a semiconductor by coating and printing. Several approaches have been presently made.

Patent document 1 discloses a pentacene thin-film formed by dispersing pentacene in an organic solvent and applying the resultant dispersion solution to a silicon substrate heated at 100° C. and formation of a transistor.

Patent document 2 discloses a method for manufacturing an organic transistor using a porphyrin compound by a coating method as mentioned above.

Patent document 3 discloses field-effect transistors using benzothieno[3,2-b][1]benzoselenophene (a compound represented by the formula (1) below wherein $X^1$ and $X^2$ are each a selenium atom; and $R^1$ and $R^2$ are each a hydrogen atom) and using an aryl derivative of benzothieno[3,2-b][1]benzothiophene (a compound represented by the formula (1) below wherein $X^1$ and $X^2$ are each a sulfur atom; and $R^1$ and $R^2$ are each a hydrogen atom).

Non-Patent document 1 discloses an organic field-effect transistor using, for example, a pentacene derivative having a specific substituent introduced therein and soluble in an organic solvent.

Non-Patent document 2 discloses a field-effect transistor using an aryl derivative of benzothieno[3,2-b][1]benzoselenophene (a compound represented by the formula (1) below wherein $X^1$ and $X^2$ are each a selenium atom; and $R^1$ and $R^2$ are each a hydrogen atom).

Non-Patent documents 3 and 4 disclose a synthesis method for an alkyl derivative of benzothieno[3,2-b][1]benzothiophene (a compound represented by the formula (1) below wherein $X^1$ and $X^2$ are each a sulfur atom; and $R^1$ and $R^2$ are each a hydrogen atom).

However, the case of a field-effect transistor using the alkyl derivative above is not known.

Patent Document 1: JP-A-2005-281180
Patent Document 2: JP-A-2005-322895
Patent Document 3: WO 2006/077888
Non-Patent Document 1: J. AM. CHEM. SOC. 2005, 127, 4986-4987
Non-Patent Document 2: J. Am. Chem. Soc. 2006, 128, 3044-3050
Non-Patent Document 3: Liquid Crystals (2003), 30(5), 603-610
Non-Patent Document 4: Collect. Czech. Chem. Commun, 67(5), 645-664, 2002

DISCLOSURE OF THE INVENTION

Problem to be Solved by the Invention

An object of the present invention is to provide a field-effect transistor excellent in stability using an organic semiconductor material soluble in an organic solvent and having a suitable property for practical printing, and further having semiconductor characteristics such as excellent carrier mobility.

Means for Solving the Problem

The present inventors have conducted studies with a view to solving the aforementioned problem. As a result, they found that manufacturing by a coating method can be made by using a compound having a specific structure as a semiconductor material, since the compound is soluble in an organic solvent and has a suitable property for printing, and that a field-effect transistor exhibiting excellent carrier mobility can be obtained. Based on the findings, the present invention was accomplished.

More specifically, according to the present invention, there are provided

[1]. A field-effect transistor characterized by containing a compound represented by the formula (1) below as a semiconductor material:

[Formula 1]

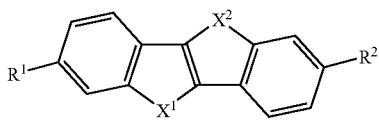

(1)

(in the formula (1), $X^1$ and $X^2$ are each independently a sulfur atom, a selenium atom or a tellurium atom; and $R^1$ and $R^2$ are each independently an unsubstituted or halogeno-substituted C1 to C36 aliphatic hydrocarbon group);

[2]. The field-effect transistor according to [1], wherein $X^1$ and $X^2$ in the formula (1) are each independently a sulfur atom or a selenium atom;

[3]. The field-effect transistor according to [1], wherein $X^1$ and $X^2$ in the formula (1) are each a sulfur atom;

[4]. The field-effect transistor according to any one of [1] to [3], wherein $R^1$ and $R^2$ in the formula (1) are each independently an unsubstituted or halogeno-substituted C2 to C24 aliphatic hydrocarbon group;

[5]. The field-effect transistor according to any one of [1] to [3], wherein $R^1$ and $R^2$ in the formula (1) are each independently an unsubstituted or halogeno-substituted C4 to C20 aliphatic hydrocarbon group;

[6]. The field-effect transistor according to any one of [1] to [3], wherein $R^1$ and $R^2$ in the formula (1) are each independently an unsubstituted aliphatic hydrocarbon group;

[7]. The field-effect transistor according to [6], wherein $R^1$ and $R^2$ in the formula (1) are each independently a saturated aliphatic hydrocarbon group;

[8]. The field-effect transistor according to [7], wherein $R^1$ and $R^2$ in the formula (1) are each independently a straight-chain aliphatic hydrocarbon group;

[9]. The field-effect transistor according to any one of [1] to [8] having a top-contact type structure, characterized in that the layer containing a compound represented by the formula (1) is provided on an insulating layer provided on a gate electrode, and further a source electrode and a drain electrode are separately provided so as to be in contact with the upper portion of the layer;

[10]. The field-effect transistor according to any one of [1] to [8], characterized in that the layer containing a compound represented by the formula (1) is provided on the electrodes of a bottom-contact type structure having an insulating layer, a gate electrode isolated by the insulating layer, and a source electrode and a drain electrode provided so as to be in contact with the insulating layer;

[11]. The field-effect transistor according to [9] or [10], characterized in that the layer containing a compound represented by the formula (1) is provided by an inkjet recording method;

[12]. Ink for manufacturing a semiconductor device characterized by containing a compound represented by the formula (1);

[13]. A method for manufacturing a field-effect transistor characterized by forming a semiconductor layer by applying the ink for manufacturing a semiconductor device according to [12] onto a substrate and drying the ink;

[14]. The method for manufacturing a field-effect transistor according to [13], characterized in that the application of ink is performed by an inkjet recording method;

[15]. The method for manufacturing a field-effect transistor according to [13] or [14], characterized by forming the semiconductor layer in the atmosphere;

[16]. The method for manufacturing a field-effect transistor according to any one of [13] to [15], characterized by performing a heat treatment after the semiconductor layer is formed;

[17]. The method for manufacturing a field-effect transistor according to [16], characterized in that temperature of the heat treatment is 40 to 120° C.;

[18]. A compound represented by the formula (2) below:

[Formula 2]

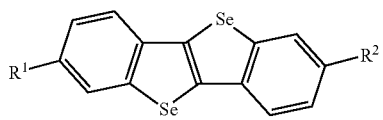

(2)

(in the formula (2), $R^1$ and $R^2$ are each independently an unsubstituted or halogeno C1 to C36 aliphatic hydrocarbon group); and

[19]. A compound represented by the formula (3) below:

[Formula 3]

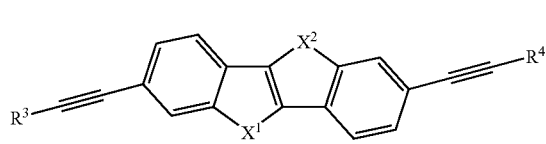

(3)

(in the formula (3), $R^3$ and $R^4$ are each independently an unsubstituted or halogeno C1 to C34 aliphatic hydrocarbon group; and $X^1$ and $X^2$ are each independently a sulfur atom, a selenium atom or a tellurium atom).

Advantage of the Invention

It was found that a field-effect transistor exhibiting excellent carrier mobility and excellent stability can be obtained by using a compound having a specific structure represented by any one of the formulas (1) to (3) above as a semiconductor material, since the compound is soluble in an organic solvent and having suitable properties for printing, enabling manufacturing by a method such as coating and printing. As a result, such an excellent field-effect transistor was successfully provided.

BEST MODE FOR CARRYING OUT THE INVENTION

The present invention will be more specifically described.
The present invention is directed to an organic field-effect transistor using a specific organic compound as a semiconductor material. As the organic compound, any one of the compounds represented by the aforementioned formulas (1) to (3) is used. The compounds represented by the formulas (1) to (3) above will be described below.

In the formula (1) or (3) above, $X^1$ and $X^2$ are each independently a sulfur atom, a selenium atom or a tellurium atom, preferably a sulfur atom or a selenium atom, and further preferably a sulfur atom.

In the formula (1) or (2) above, $R^1$ and $R^2$ are each independently an unsubstituted or halogeno-substituted C1 to C36 aliphatic hydrocarbon group.

As the aliphatic hydrocarbon group, a saturated or unsaturated and straight, branched or cyclic aliphatic hydrocarbon group may be mentioned. Preferably, a straight or branched aliphatic hydrocarbon group, and further preferably a straight aliphatic hydrocarbon group may be mentioned.

The number of carbon atoms is usually C1 to C36, preferably C2 to C24, and further preferably C4 to C20.

Examples of the straight or branched saturated aliphatic hydrocarbon group include methyl, ethyl, propyl, iso-propyl, n-butyl, iso-butyl, t-butyl, n-pentyl, iso-pentyl, t-pentyl, sec-pentyl, n-hexyl, iso-hexyl, n-heptyl, sec-heptyl, n-octyl, n-nonyl, sec-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, docosyl, n-pentacosyl, n-octacosyl, n-tricontyl, 5-(n-pentyl)decyl, heneicosyl, tricosyl, tetracosyl, hexacosyl, heptacosyl, nonacosyl, n-triacontyl, squaryl, dotriacontyl and hexatriacontyl.

Also, examples of the cyclic saturated aliphatic hydrocarbon group include cyclohexyl, cyclopentyl, adamantyl and norbornyl.

Examples of the straight or branched unsaturated aliphatic hydrocarbon group include vinyl, allyl, eicosadienyl, 11,14-eicosadienyl, geranyl(trans-3,7-dimethyl-2,6-octadien-1-yl), farnesyl(trans,trans-3,7,11-trimethyl-2,6,10-dodecatrien-1-yl), 4-pentenyl, 1-propynyl, 1-hexynyl, 1-octynyl, 1-decynyl, 1-undecynyl, 1-dodecynyl, 1-tetradecynyl, 1-hexadecynyl and 1-nonadecynyl.

Of the straight, branched and cyclic aliphatic hydrocarbon groups, straight or branched groups are preferred and straight groups are further preferred.

The saturated or unsaturated aliphatic hydrocarbon group includes alkyl representing a saturated group, alkenyl containing a carbon-carbon double bond and alkynyl containing a carbon-carbon triple bond. As the residue of the aliphatic hydrocarbon group, combinations of these groups including, i.e., an aliphatic hydrocarbon group partly containing a carbon-carbon double bond and a carbon-carbon triple bond at the same time are all included. More preferably, alkyl or alkynyl, and further preferably alkyl may be mentioned.

In the case where the residue of an aliphatic hydrocarbon group represented by $R^1$ or $R^2$ in the formula (1) or (2) above is an unsaturated aliphatic hydrocarbon group, it is further preferred that the unsaturated carbon-carbon bond is present at a site conjugated with the benzene ring having a substituent of $R^1$ or $R^2$, in other words, one of the carbon atoms of the unsaturated carbon-carbon bond is directly bonded to the benzene ring. Also in this case, similarly to the above case, alkynyl is more preferable than alkenyl.

The halogeno-substituted aliphatic hydrocarbon group refers to an aliphatic hydrocarbon group as mentioned above substituted with an arbitrary number and type(s) of halogen atom(s) at an arbitrary position(s).

As the type of halogen atom, fluorine, chlorine, bromine and iodine are preferably mentioned. More preferably fluorine, chlorine and bromine, and further preferably fluorine or bromine may be mentioned.

Specific examples of the halogeno-substituted aliphatic hydrocarbon group include chloromethyl, bromomethyl, trifluoromethyl, pentafluoroethyl, n-perfluoropropyl, n-perfluorobutyl, n-perfluoropentyl, n-perfluorooctyl, n-perfluorodecyl, n-(dodecafluoro)-6-iodohexyl, 2,2,3,3,3-pentafluoropropyl and 2,2,3,3-tetrafluoropropyl.

In the formula (3) above, the unsubstituted or halogeno-substituted aliphatic hydrocarbon group represented by each of $R^3$ and $R^4$ is a group in which a carbon atom binding to a benzene ring and a carbon atom binding to the carbon atom form a carbon-carbon triple bond at $R^1$ and $R^2$ of a compound represented by the formula (1) or (2) above. Accordingly, as specific examples of the aliphatic hydrocarbon group represented by each of $R^3$ and $R^4$, the same groups as exemplified as $R^1$ and $R^2$ may be mentioned as long as they have C1 to C34.

Also, as a preferable group thereof, the same groups as long as they are constituted of C1 to C34 may be mentioned.

The compounds represented by the formula (1) above can be synthesized by a known method described, for example, in NON-PATENT DOCUMENT 2 and also obtained in accordance with the method described, for example, in PATENT DOCUMENT 3.

To describe more specifically, a halogenated compound such as a compound represented by the formula (4) below, for example, an iodide compound, serving as a raw material is reacted with an acetylene derivative to perform a coupling reaction to obtain a compound of the formula (3) above.

Further, the compound of the formula (3) thus obtained is reduced (hydrogenated) in accordance with a customary method to obtain a compound represented by the formula (1) above where $R^1$ or $R^2$ is an unsaturated aliphatic hydrocarbon group (alkenyl) or a saturated aliphatic hydrocarbon group (alkyl). If a compound represented by the formula (3) above where $X^1$ and $X^2$ are each a selenium atom is used, a compound of the formula (2) above can be obtained in the same manner.

The formula (3) below shows a coupling reaction between a compound of the formula (4) below and an acetylene derivative. However, a coupling reaction with an ethylene derivative proceeds similarly. In this case, an alkenyl derivative can be obtained having a carbon-carbon double bond in place of the carbon-carbon triple bond of the formula (3) below. The alkenyl compound is included in the compounds of the formula (1) above.

If the reductive reaction conditions for a compound of the formula (3) below, more specifically, the type and amount of reaction reagent to be used in the reductive reaction, a reaction solvent and a combination of these, are appropriately selected, the reductive reaction is allowed to proceed until a carbon-carbon double bond is obtained and stopped at this stage, or allowed to proceed until a saturated aliphatic hydrocarbon is obtained.

[Formula 4]

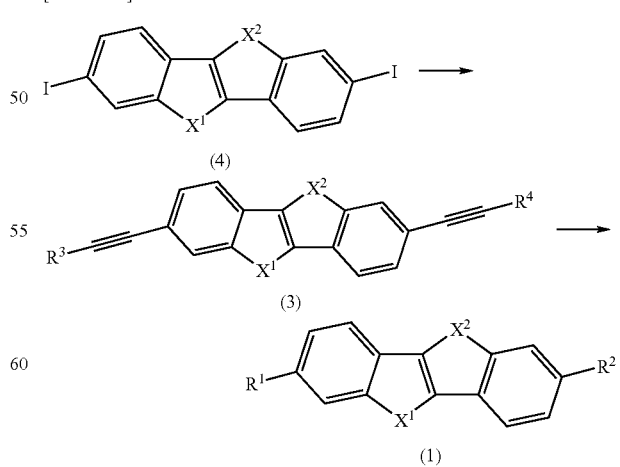

(In the compound represented by the formula (4), $X^1$ and $X^2$ are the same as defined in the formula (1) above).

The method for purifying the compounds represented by the formulas (1) to (3) above is not particularly limited. Known methods such as recrystallization, column chromatography and vacuum sublimation purification may be employed. These methods may be used in combination if needed.

Specific examples of the compounds represented by the formulas (1) to (3) above are shown in Table 1 below.

TABLE 1

| Compund No. | $X^1$ | $X^2$ | $R^1$ | $R^2$ |
|---|---|---|---|---|
| 1 | S | S | CH3 | CH3 |
| 2 | S | S | C2H5 | C2H5 |
| 3 | S | S | n-C3H7 | n-C3H7 |
| 4 | S | S | iso-C3H7 | iso-C3H7 |
| 5 | S | S | n-C4H9 | n-C4H9 |
| 6 | S | S | iso-C4H9 | iso-C4H9 |
| 7 | S | S | t-C4H9 | t-C4H9 |
| 8 | S | S | n-C5H11 | n-C5H11 |
| 9 | S | S | iso-C5H11 | iso-C5H11 |
| 10 | S | S | t-C5H11 | t-C5H11 |
| 11 | S | S | sec-C5H11 | sec-C5H11 |
| 12 | S | S | n-C6H13 | n-C6H13 |
| 13 | S | S | iso-C6H13 | iso-C6H13 |
| 14 | S | S | n-C7H15 | n-C7H15 |
| 15 | S | S | sec-C7H15 | sec-C7H15 |
| 16 | S | S | n-C8H17 | n-C8H17 |
| 17 | S | S | n-C9H19 | n-C9H19 |
| 18 | S | S | n-C10H21 | n-C10H21 |
| 19 | S | S | n-C11H23 | n-C11H23 |
| 20 | S | S | n-C12H25 | n-C12H25 |
| 21 | S | S | n-C13H27 | n-C13H27 |
| 22 | S | S | n-C14H29 | n-C14H29 |
| 23 | S | S | n-C15H31 | n-C15H31 |
| 24 | S | S | n-C16H33 | n-C16H33 |
| 25 | S | S | n-C17H35 | n-C17H35 |
| 26 | S | S | n-C18H37 | n-C18H37 |
| 27 | S | S | n-C19H39 | n-C19H39 |
| 28 | S | S | n-C20H41 | n-C20H41 |
| 29 | S | S | n-C21H43 | n-C21H43 |
| 30 | S | S | n-C22H45 | n-C22H45 |
| 31 | S | S | n-C23H47 | n-C23H47 |
| 32 | S | S | n-C24H49 | n-C24H49 |
| 33 | S | S | n-C25H51 | n-C25H51 |
| 34 | S | S | n-C30H61 | n-C30H61 |
| 35 | S | S | n-C35H71 | n-C35H71 |
| 36 | S | S | n-C36H73 | n-C36H73 |
| 37 | S | S | C5H9(C5H11)2 | C5H9(C5H11)2 |
| 38 | S | S | n-C9H19 | sec-C9H19 |
| 39 | S | S | n-C6H13 | sec-C9H19 |
| 40 | S | S | n-C8H17 | n-C10H21 |
| 41 | S | S | n-C8H17 | n-C12H25 |
| 42 | Se | Se | sec-C5H11 | sec-C5H11 |
| 43 | Se | Se | n-C6H13 | n-C6H13 |
| 44 | Se | Se | iso-C6H13 | iso-C6H13 |
| 45 | Se | Se | n-C7H15 | n-C7H15 |
| 46 | Se | Se | sec-C7H15 | sec-C7H15 |
| 47 | Se | Se | n-C8H17 | n-C8H17 |
| 48 | Se | Se | n-C9H19 | n-C9H19 |
| 49 | Se | Se | n-C10H21 | n-C10H21 |
| 50 | Se | Se | n-C11H23 | n-C11H23 |
| 51 | Se | Se | n-C12H25 | n-C12H25 |
| 52 | Se | Se | n-C13H27 | n-C13H27 |
| 53 | Se | Se | n-C14H29 | n-C14H29 |
| 54 | Se | Se | n-C16H33 | n-C16H33 |
| 55 | Se | Se | n-C18H37 | n-C18H37 |
| 56 | Se | Se | n-C9H19 | sec-C9H19 |
| 57 | Se | Se | n-C8H17 | n-C12H25 |
| 58 | Se | Se | n-C4H9 | n-C12H25 |
| 59 | Te | Te | n-C8H17 | n-C8H17 |
| 60 | Te | Te | n-C9H19 | n-C9H19 |
| 61 | Te | Te | n-C10H21 | n-C10H21 |
| 62 | Te | Te | n-C11H23 | n-C11H23 |
| 63 | Te | Te | n-C12H25 | n-C12H25 |
| 64 | S | Se | n-C8H17 | n-C8H17 |
| 65 | S | Se | n-C9H19 | n-C9H19 |
| 66 | S | Te | n-C10H21 | n-C10H21 |
| 67 | Se | Te | n-C11H23 | n-C11H23 |
| 68 | S | Se | n-C12H25 | n-C12H25 |
| 69 | S | S | n-C8H16Cl | n-C8H16Cl |
| 70 | S | S | n-C8H16Br | n-C8H16Br |
| 71 | S | S | CH2Cl | CH2Cl |
| 72 | S | S | CH2Br | CH2Br |
| 73 | S | S | CF3 | CF3 |
| 74 | S | S | C2F5 | C2F5 |
| 75 | S | S | C3F7 | C3F7 |
| 76 | S | S | C4F9 | C4F9 |
| 77 | S | S | C5F11 | C5F11 |
| 78 | S | S | C8F17 | C8F17 |
| 79 | S | S | C10F21 | C10F21 |
| 80 | S | S | C6F12I | C6F12I |
| 81 | S | S | —CH2C2F5 | —CH2C2F5 |
| 82 | S | S | —CH2CF2CHF2 | —CH2CF2CHF2 |
| 83 | S | S | —CH=CH2 | —CH=CH2 |
| 84 | S | S | —CH2CH=CH2 | —CH2CH=CH2 |
| 85 | S | S | —C4H8CH=CH2 | —C4H8CH=CH2 |
| 86 | S | S | —C≡CC2H5 | —C≡CC2H5 |
| 87 | S | S | —C≡CC4H9 | —C≡CC4H9 |
| 88 | S | S | —C≡CC6H13 | —C≡CC6H13 |
| 89 | S | S | —C≡CC8H17 | —C≡CC8H17 |
| 90 | S | S | —C≡CC9H19 | —C≡CC9H19 |
| 91 | S | S | —C≡CC10H21 | —C≡CC10H21 |
| 92 | S | S | —C≡CC12H25 | —C≡CC12H25 |
| 93 | S | S | —C≡CC14H29 | —C≡CC14H29 |
| 94 | S | S | —C≡CC17H35 | —C≡CC17H35 |
| 95 | Se | Se | —C≡CC6H13 | —C≡CC6H13 |
| 96 | Se | Se | —C≡CC8H17 | —C≡CC8H17 |
| 97 | Se | Se | —C≡CC10H21 | —C≡CC10H21 |
| 98 | S | S | cycloC5H9 | cycloC5H9 |
| 99 | S | S | cycloC6H11 | cycloC6H11 |

The field-effect transistor (hereinafter sometimes referred to as "FET") of the present invention has two electrodes, namely, a source electrode and a drain electrode, in contact with the semiconductor. The current flowing between these electrodes is controlled by the voltage to be applied to another electrode called a gate electrode.

Generally, as the field-effect transistor, a structure called a metal-insulator-semiconductor (MIS) structure where the gate electrode is isolated by the insulating film is frequently used. The structure where a metal oxide film is used as the insulating film is called a MOS structure. Besides these, there is a structure (MES structure) where the gate electrode is formed via the Schottky barrier. However, the MIS structure is frequently used in the FET using an organic semiconductor material.

Referring to the accompanying drawings, the field-effect transistor of the present invention will be more specifically described below; however, the structure of the present invention is not limited to these structures.

FIG. 1 shows examples illustrating several embodiments of the field-effect transistor of the present invention. In each example, reference numeral 1 represents a source electrode, 2 a semiconductor layer, 3 a drain electrode, 4 an insulating layer, 5 a gate electrode and 6 a substrate, respectively. Note that the arrangement of individual layers and electrodes may be appropriately selected depending upon the use of the device. Embodiments A to D are called horizontal FETs since current flows in parallel to the substrate. Embodiment A is called a bottom contact structure, and Embodiment B is called a top contact structure. Embodiment C shows a structure frequently used in forming an FET of an organic single crystal, having source and drain electrodes and an insulating layer formed on the semiconductor layer and a gate electrode formed on the insulating layer. Embodiment D is called a top & bottom type transistor. Embodiment E shows a schematic view of an FET having a vertical structure, in other words, a static induction transistor (SIT). According to the SIT structure, since current spreads over the plain, a large amount of carriers can be migrated at a time. In addition, since the source electrode and the drain electrode are arranged vertically, the distance between the electrodes can be reduced and thereby high response can be realized. Accordingly, this can be preferably applied to the use for supplying a large amount of current or performing high-speed switching. Note that the substrate is not shown in Embodiment E of FIG. 1, generally, a substrate are provided outside the source and drain electrodes represented by reference numerals 1 and 3 in FIG. 1E.

Individual components of each embodiment will be described.

It is necessary for the substrate 6 to hold individual layers formed thereon without removing. For example, insulating materials such as a resin board, film, paper, glass, quartz and ceramic; conductive layers formed of e.g., a metal and an alloy having an insulating layer formed thereon by coating and materials formed of resins and inorganic materials in various combinations can be used. Examples of the resin film that can be used include polyethylene terephthalate, polyethylene naphthalate, polyethersulfone, polyamide, polyimide, polycarbonate, cellulose triacetate and polyetherimide. When a resin film or paper is used, a flexible semiconductor device can be resulted. The semiconductor device becomes flexible, light and improved in applicability. The thickness of the substrate is usually 1 μm to 10 mm, and preferably 5 μm to 5 mm.

A material having conductivity is used in the source electrode 1, the drain electrode 3 and the gate electrode 5. For example, metals such as platinum, gold, silver, aluminum, chromium, tungsten, tantalum, nickel, cobalt, copper, iron, lead, tin, titanium, indium, palladium, molybdenum, magnesium, calcium, barium, lithium, potassium and sodium, and alloys containing these metals; conductive oxides such as $InO_2$, $ZnO_2$, $SnO_2$ and ITO; conductive polymer compounds such as polyaniline, polypyrrol, polythiophene, polyacetylene, poly(para-phenylene vinylene) and polydiacetylene; semiconductors such as silicon, germanium and gallium arsenic; and carbon materials such as carbon black, fullerene, carbon-nanotube and graphite can be used. In addition, the conductive polymer compounds and semiconductors may have a dopant. As the dopant used herein acids such as hydrochloric acid, sulfuric acid and sulfonic acid; Lewis acids such as $PF_5$, $AsF_5$ and $FeCl_3$, halogen atoms such as iodine; and metal atoms such as lithium, sodium and potassium can be used. Also, conductive complex materials having carbon black and metal particles such as gold, platinum, silver and copper dispersed in the aforementioned materials can be used.

To each of the electrodes 1, 3 and 5, wiring is connected. The wiring may be formed of the same material as used in the electrode.

As the insulating layer 4, a material having insulating properties can be used. For example, polymers such as polyparaxylylene, polyacrylate, polymethylmethacrylate, polystyrene, polyvinylphenol, polyamide, polyimide, polycarbonate, polyester, polyvinyl alcohol, polyvinyl acetate, polyurethane, polysulfone, an epoxy resin and a phenolic resin, and copolymers formed of these in combination; oxides such as silicon dioxide, alumina oxide, titanium oxide and tantalum oxide; ferroelectric oxides such as $SrTiO_3$ and $BaTiO_3$: nitrides such as silicon nitride and aluminum nitride; sulfides; and dielectric substances such as fluorides, or polymers having particles of these dielectric substances dispersed therein can be used. The film thickness of the insulating layer 4 varies depending upon the material; however, it is usually 0.1 nm to 100 μm, preferably 0.5 nm to 50 μm, and more preferably 5 nm to 10 μm.

As the material for the semiconductor layer 2, compounds represented by the formulas (1) to (3) above can be used. Of the compounds represented by e.g., the formula (1), alkyl derivatives are more preferable than alkenyl derivatives and alkynyl derivatives, as the material for the semiconductor.

As the material for the semiconductor layer 2, several types of compounds represented by the formulas (1) to (3) above may be used in combination; however, it is necessary to contain the compounds represented by the formulas (1) to (3) in the total amount of 50 wt % or more, preferably 80 wt % or more, and further preferably 95% or more. To improve the properties of a field-effect transistor and give another property to the transistor, another organic semiconductor material and various types of additives may be added, if needed. Alternatively, the semiconductor layer 2 may be formed of a plurality of layers.

The thinner the film thickness of the semiconductor layer 2, the more preferable as long as it maintains necessary functions. In the horizontal field-effect transistor shown in A, B and D, as long as the film thickness is a predetermined value or more, the properties of the semiconductor device do not vary depending upon the film thickness. On the other hand, when the thickness of the film increases, current leakage increases in most cases. For the reason, the film thickness preferably falls within an appropriate range. The film thickness of the semiconductor layer in order for the semiconductor to show necessary functions is usually 0.1 nm to 10 μm, preferably 0.5 nm to 5 μm, and more preferably 1 nm to 3 μm.

The field-effect transistor of the present invention may employ another type of layer between individual layers mentioned above and the outer surface of the semiconductor device, if needed. For example, if a protective layer is formed directly or via the other type of layer on the semiconductor layer, the effect of the outside air such as humidity can be reduced. Besides this, the ON/OFF ratio of the device can be increased. Likewise, electrical properties can be advantageously stabilized.

The materials of the protective layer are not particularly limited. For example, films formed of various types of reins such as an epoxy resin, an acrylic resin including polymethyl methacrylate, polyurethane, polyimide, polyvinyl alcohol, a fluorine resin and polyolefin, dielectric films such as inorganic oxide films formed of silicon oxide, aluminum oxide and silicon nitride, and a nitride film are preferably used. In particular, a resin (polymer) having low permeability of oxygen and moisture and low water absorption is preferred. A protective material recently developed for an organic EL display can be used. The film thickness of the protective layer may be arbitrarily set depending upon the purpose and is usually 100 nm to 1 mm.

Furthermore, the characteristics of the device can be improved by previously applying a surface treatment onto the substrate or insulating layer on which a semiconductor layer is to be layered. For example, when the degree of hydrophilicity/hydrophobicity of the substrate surface is controlled, the quality of the film that is to be formed on the substrate can be improved. In particular, the characteristics of an organic semiconductor material may sometimes greatly varied by the state of the film such as molecular orientation. Therefore, when the molecular orientation of the interface portion between e.g., the substrate and the semiconductor layer to be formed later is controlled and the number of trapping sites present on a substrate and an insulating layer is reduced by the surface treatment applied to e.g., the substrate, the characteristics such as carrier mobility is conceivably improved. The trapping site refers to a functional group such as a hydroxyl group present in an untreated substrate. When such a functional group is present, electrons are attracted to the functional group, with the result that carrier mobility decreases. Therefore, it is mostly effective to reduce the number of trapping sites in improving the characteristics such as carrier mobility. Examples of such a substrate treatment include a hydrophobizing treatment with hexamethyldisilazane, cyclohexene or octadecyl trichlorosilane; an acid treatment with e.g., hydrochloric acid, sulfuric acid or acetic acid; an alkali treatment with e.g., sodium hydroxide, potassium hydroxide, calcium hydroxide or ammonia; an ozone treatment; a fluorination treatment; a plasma treatment with e.g., oxygen or argon; a treatment with formation of a Langmuir-Blodgett film; a treatment with thin-film formation such as another type of insulating film or semiconductor film; a mechanical treatment; an electrical treatment such as corona discharge; and a rubbing treatment with e.g., fiber.

As a method for providing individual layers in these embodiments, for example, a vacuum deposition method, a sputtering method, a coating method, a printing method and a sol-gel method may be appropriately employed. In consideration of problems such as cost and labor, a coating method and a printing method using inkjet printing are preferred.

Next, a method for manufacturing the field-effect transistor of the present invention will be described by way of a bottom-contact type field-effect transistor (FET) shown in Embodiment A of FIG. 1 and with reference to FIG. 2.

This manufacturing method can be similarly applied to a field-effect transistor of other embodiments.

(Substrate and Substrate Treatment)

The field-effect transistor of the present invention is formed by providing various types of requisite layers and electrodes on a substrate 6 (see FIG. 2 (1)). As the substrate, the aforementioned substrates can be used. To the substrate, the aforementioned surface treatment can be also applied. The thickness of the substrate 6 is preferably as thin as possible as long as a necessary function is not inhibited. Although the thickness varies depending upon the material, it is generally 1 µm to 10 mm and preferably 5 µm to 5 mm. Furthermore, if necessary, the substrate may have a function of an electrode.

(Formation of a Gate Electrode)

A gate electrode 5 is formed on the substrate 6 (see FIG. 2 (2)). As the material for the electrode, the aforementioned materials can be used. As a method for forming an electrode film, various types of methods can be used. For example, a vacuum deposition method, a sputtering method, a coating method, a heat-transfer method, a printing method and a sol-gel method can be employed. It is preferred to perform patterning so as to obtain a desired shape, if needed, during and after the film formation process. Various types of patterning methods may be employed. For example, a photolithography may be mentioned which is a combination of patterning and etching of a photoresist. Alternatively, patterning can be performed also by a printing method such as an inkjet printing, a screen printing, an off-set printing or a relief printing; soft lithography such as micro-contact printing; and a method using a plurality of these methods in combination. The thickness of the gate electrode 5 varies depending upon the material; however, it is generally 0.1 nm to 10 µm, preferably 0.5 nm to 5 µm and more preferably 1 nm to 3 µm. When the gate electrode also serves as the substrate, the thickness of the gate electrode may be larger than the aforementioned value.

(Formation of Insulating Layer)

An insulating layer 4 is formed on the gate electrode 5 (see FIG. 2 (3)). As the insulating materials, the aforementioned ones may be used. Various types of methods can be used for forming the insulating layer 4. For example, coating methods such as spin coating, spray coating, dip coating, casting, bar coating and blade coating; printing methods such as screen printing, off-set printing and inkjet printing; and dry processing methods such as a vacuum deposition method, a molecular-beam epitaxial growth method, an ion-cluster beam method, an ion-plating method, a sputtering method, an atmospheric plasma method and a CVD method may be mentioned. Beside these, a sol-gel method and a method of forming an oxide film on a metal, like alumite formed on aluminum, may be employed.

Note that in the portion at which the insulating layer is in contact with a semiconductor layer, a predetermined surface treatment can be also applied to the insulating layer in order to properly orient the molecules constituting a semiconductor at the interface between both layers, for example, molecules of a compound represented by any one of the formulas (1) to (3) above. As the surface treatment, the same surface treatments as those to be applied to the substrate surface can be used. The film thickness of the insulating layer 4 is as thin as possible as long as its function is not inhibited. The thickness is usually 0.1 nm to 100 µm, preferably 0.5 nm to 50 µm, and more preferably 5 nm to 10 µm.

(Formation of Source Electrode and Drain Electrode)

The source electrode 1 and drain electrode 3 can be formed in the same manner as used in forming the gate electrode 5 (see FIG. 2 (4)).

(Formation of Semiconductor Layer)

As materials for a semiconductor, an organic material containing the compounds represented by the formulas (1) to (3) or several types of compound mixtures containing these compounds, in a total amount of not less than 50% by weight, can be used. A semiconductor layer can be formed by several types of film-forming methods, which can be roughly classified into a forming method by a vacuum process such as a sputtering method, a CVD method, a molecular beam epitaxial method or a vacuum deposition method and a forming method by a solution process such as a coating method including a dip coat method, a die coater method, a roll coater method, a bar coater method or a spin coat method, an inkjet method, a screen printing method, an off-set printing method or a micro-contact printing method. The forming methods for a semiconductor layer will be more specifically described below.

First, a method for obtaining an organic semiconductor layer by forming an organic material into a film by a vacuum process will be described.

An organic material as mentioned above is heated under vacuum in a crucible or a metal boat, and the vaporized organic material is allowed to adhere (deposit) on a substrate (exposed portions of the insulating layer, the source electrode and the drain electrode). This method (vapor deposition method) is preferably employed. The degree of vacuum in this case is usually $1.0 \times 10^{-1}$ Pa or less and preferably $1.0 \times 10^{-4}$ Pa or less. Furthermore, since the characteristics of the organic semiconductor layer (film) leading to the characteristics of the field-effect transistor are varied depending upon the substrate temperature during the deposition process, it is preferred that the substrate temperature is carefully selected. The substrate temperature during the deposition process is usually 0 to 200° C. and preferably 10 to 150° C. and the deposition rate is usually 0.001 nm/second to 10 nm/second, and preferably 0.01 nm/second to 1 nm/second. The film thickness of the organic semiconductor layer formed of an organic material is usually 0.1 nm to 10 μm, preferably 0.5 nm to 5 μm, and more preferably 1 nm to 3 μm.

Note that a sputtering method, in which a target material is bombarded with accelerated ions such as argon ions and atoms of the target material thus ejected are allowed to deposit on a substrate, may be used in place of the deposition method, in which an organic material for forming an organic semiconductor layer is heated to vaporize and deposited on a substrate.

Next, a method for obtaining an organic semiconductor layer by forming a film of an organic semiconductor material by a solution process will be described. Since a semiconductor material according to the present invention is easily dissolved in an organic solvent, it is possible to obtain practical semiconductor characteristics by the solution process. In the manufacturing method by coating, since it is not necessary to form vacuum or set the ambient conditions at high temperature, a large-area field-effect transistor can be manufactured at low cost. Therefore, this method is advantageous and preferable among various types of manufacturing methods for a semiconductor layer.

First, compounds represented by the formulas (1) to (3) are dissolved in a solvent to prepare ink for manufacturing a semiconductor device. The solvent to be used herein is not particularly limited as long as the compounds can be dissolved and a film can be formed on a substrate. As the solvent, an organic solvent is preferred. Specific examples thereof that can be used include halogeno-hydrocarbon solvents such as chloroform, methylene chloride and dichloroethane; alcohol solvents such as methanol, ethanol, isopropanol and butanol; fluoroalcohols such as octafluoro pentanol and pentafluoro propanol; ester solvents such as ethyl acetate, butyl acetate, ethyl benzoate and diethyl carbonate; aromatic hydrocarbon solvents such as toluene, xylene, benzene, chlorobenzene and dichlorobenzene; ketone solvents such as acetone, methylethyl ketone, methylisobutyl ketone, cyclopentanone and cyclohexanone; amide solvents such as dimethyl formamide, dimethyl acetamide and N-methylpyrrolidone; and ether solvents such as tetrahydrofuran and diisobutyl ether. These can be used singly or as a mixture.

The concentration of the sum of the compounds represented by the formulas (1) to (3) above or a mixture thereof in ink varies depending upon the type of solvent and the film thickness of the semiconductor layer to be manufactured; however, it is about 0.001% to 50% and preferably about 0.01% to 20%.

For improving the film-formability of the semiconductor layer or for doping (described later), additives and other types of semiconductor materials can be blended.

In the case of using the ink, materials including a semiconductor material are dissolved in the aforementioned solvent, and if necessary, subjected to a heat dissolution process. Furthermore, the resultant solution is filtrated by a filter to remove solid substances including impurities. In this manner, ink for forming a semiconductor device can be obtained. Use of such ink is preferable in manufacturing a semiconductor layer, because the film-formability of the semiconductor layer is improved.

Note that if the ink of the present invention is used, patterning and circuit formation of a semiconductor can be performed by an inkjet recording method.

The ink for manufacturing a semiconductor device prepared as mentioned above is applied to a substrate (exposed portions of the insulating layer, the source electrode and the drain electrode). The coating methods that can be employed herein include coating methods such as casting, spin coating, dip coating, blade coating, wire-bar coating and spray coating; printing methods such as inkjet printing, screen printing, off-set printing, relief printing and gravure printing; and soft lithographic methods such as a micro-contact printing method. Besides these, a method employing these methods in combination can be adopted. Furthermore, as an analogous method to the coating method, for example, the Langmuir-Blodgett method, in which a single-molecule film of a semiconductor layer is formed by adding the aforementioned ink dropwise onto a water surface and transferred and stacked onto a substrate; and a method of sandwiching a liquid crystal material and a melt-state material between two substrates or introducing such a material between the substrates by a capillary phenomenon can be employed. The film thickness of the organic semiconductor layer prepared by the aforementioned methods is preferably as thin as possible as long as its function is not inhibited. When the film thickness increases, current leakage may increase. The film thickness of the organic semiconductor layer is usually 0.1 nm to 10 μm, preferably 0.5 nm to 5 μm, and more preferably 1 nm to 3 μm.

The semiconductor layer (see FIG. 2 (5)) thus manufactured can be further improved in characteristics by post treatment. For example, it is considered that heat treatment may relax distortion in the film produced during a film-forming process, reduce the number of pin holes, etc., and control alignment/orientation in the film. By virtue of these, the characteristics of a semiconductor can be improved and stabilized. When the field-effect transistor of the present invention is formed, it is effective to perform the heat treatment for improving the characteristics thereof. The heat treatment is performed by heating a substrate after a semiconductor layer is formed. The temperature of the heat treatment is not particularly limited; however, it is usually room temperature to about 150° C., preferably 40° C. to 120° C., and further preferably 45° C. to 100° C. The time for the treatment is not particularly limited; however, it is usually from 1 minute to 24 hours, and preferably 2 minutes to about 3 hours. The treatment may be performed in the atmosphere such as the air or an inert atmosphere such as nitrogen or argon.

The heat treatment may be applied at any stage as long as a semiconductor layer is already formed. For example, in the case of a top-contact type transistor, the heat treatment may be performed after the electrode(s) are formed following formation of the semiconductor layer or before the electrode(s) are formed.

As another post treatment method for a semiconductor layer, a treatment with an oxidative or reducible gas such as oxygen or hydrogen or an oxidative or reducible liquid may be mentioned. The oxidation or reduction can induce a change in characteristics. This is used in order to increase or decrease the carrier density of the film.

The compounds represented by the formula (1) above to be used in the field-effect transistor of the present invention have different melting points depending upon the lengths of the aliphatic hydrocarbon groups represented by $R^1$ and $R^2$ and further optionally have two thermal phase transition points. The melting points may be visually measured by use of e.g., a hot-plate type melting-point measurer manufactured by Yanagimoto Mfg. Co., Ltd. in accordance with a customary method. Furthermore, the thermal phase transition point can be determined by differential thermal analysis using a machine such as DSC6200 manufactured by Seiko Instruments Inc.

In the compound represented by the formula (1) above and having no thermal phase transition point, the upper limit of the heat treatment temperature is not more than the melting initiation temperature of the compound and the lower limit thereof is usually room temperature or more, preferably 45° C. or more, further preferably 80° C. or more, and particularly preferably 100° C. or more. Since the upper limit of the heat treatment temperature varies depending upon the compound represented by the formula (1) to be used in a transistor, it is difficult to generalize; however, the aforementioned range is mostly applied.

In the case where a compound represented by the formula (1) above has two thermal phase transition points (thermal phase transition temperatures), it is satisfactory the heat treatment is performed within the temperature range between the two thermal phase transition points, that is, within the temperature range between not less than the lower thermal phase transition point and not more than the higher thermal phase transition point. Since the temperature range varies depending upon the compound represented by the formula (1) above to be used in a transistor, it is difficult to generalize; however, an approximate range is from not less than 80° C. to not more than 150° C., preferably from not less than 80° C. to not more than 130° C., and more preferably from not less than 100° C. to not more than 130° C.

It is more important to determine which temperature the heat treatment is performed rather than which stage the heat treatment is performed. As described above, more excellent semiconductor characteristics tend to be obtained by the heat treatment performed at an appropriate temperature than by the heat treatment similarly performed at an inappropriate temperature. In some cases, charge mobility is improved several fold to 10 fold or more.

The semiconductor characteristics can be changed by adding an extremely small amount of element, atomic group, molecule and/or polymer by a technique called doping. For example, oxygen and hydrogen and the like, acids such as hydrochloric acid, sulfuric acid and sulfonic acid, Lewis acids such as $PF_5$, $AsF_5$ and $FeCl_3$, halogen atoms such as iodine, and metal atoms such as sodium and potassium can be doped. This doping can be attained by exposing a semiconductor layer to gases of these, by dipping a semiconductor layer in solutions of these or by applying an electrochemical doping treatment to a semiconductor layer. Doping of these is not necessary to perform after formation of the semiconductor layer. These may be added during the synthesis of a semiconductor material. When a semiconductor layer is manufactured by a process using ink for manufacturing a semiconductor device, these may be added to the ink. Alternatively, these can be added at the stage, e.g., in a step of forming a precursor thin film as disclosed, for example, in PATENT DOCUMENT 2. Furthermore, the materials to be used in doping may be added to a material for forming a semiconductor layer during a deposition process and simultaneously deposited, or mixed with the ambient atmosphere of a process for forming a semiconductor layer (a semiconductor layer is manufactured under the atmosphere containing a doping material). Moreover, doping can be also performed by accelerating ions under vacuum and bombarding a film with the accelerated ions.

As the effect of doping thus carried out, for example, a change of electrical conductivity due to an increase or decrease of carrier density, a polarity change of carriers (p type, n-type) and a change of the Fermi level may be mentioned. Such doping is frequently used in semiconductor devices using an inorganic material particularly silicon and the like.

(Protective Layer)

A protective layer 7 is formed on the semiconductor layer. It is advantageous because the effect of the outer air can be reduced to a minimum and the electrical properties of an organic field-effect transistor can be stabilized (see FIG. 2 (6)). As the protective materials, the aforementioned ones may be used.

The film thickness of the protective layer 7 can be arbitrarily set depending upon its purpose; however it is usually 100 nm to 1 mm.

Various methods can be employed in forming a protective layer. When the protective layer is made of a resin, a method of applying a solution containing the resin and drying it to obtain a resin film and a method of applying or depositing monomers of the resin and then polymerizing the monomers, may be mentioned. After the film-formation, a crosslinking treatment may be performed. When the protective layer is formed of an inorganic material, for example, a forming method performed in a vacuum process such as a sputtering method or a deposition method and a forming method performed in a solution process such as a sol-gel method can be also employed.

In the field-effect transistor of the present invention, a protective layer may be provided not only on a semiconductor layer but also between individual layers if needed. Such a protective layer may sometimes play a role in stabilizing the electrical properties of an organic field-effect transistor.

In the present invention, since an organic material is used as a semiconductor material, manufacturing can be made at a relatively low temperature. Accordingly, flexible materials such as a plastic plate and a plastic film, which cannot be used in the conditions exposed to high temperature, can be used as a substrate. As a result, a device light, excellent in flexibility and rarely broken can be manufactured and can be used as a switching device, etc. for an active matrix of a display. As the display, for example, a liquid crystal display, a polymer dispersed liquid crystal display, an electrophoretic display, an EL display, an electrochromic display and a particle rotation display can be mentioned. In addition, since the field-effect transistor of the present invention can be manufactured by a solution process such as coating, it is suitable for manufacturing a large-area display compared to the material which cannot be manufactured if a vacuum process such as deposition is not used. The field-effect transistor can be obtained at extremely low cost compared to a conventional one.

The field-effect transistor of the present invention can be used also as a digital device such as a memory circuit device, a signal driver circuit device and a signal processing circuit device, and an analog device. Furthermore, these are used in combination to manufacture an IC card and an IC tag. In addition, when the field-effect transistor of the present invention is stimulated by an external stimulant such as a chemical substance, the characteristics of the transistor can be changed. Therefore, the field-effect transistor can be used also as an FET sensor.

The operational characteristics of the field-effect transistor are determined by the carrier mobility and conductivity of the semiconductor layer, the electrostatic capacity of the insulating layer and the structure of the device (the distance and width between the source and drain electrodes, the film thickness of the insulating layer, etc.). Of the semiconductor materials that are used in the field-effect transistor, a semiconductor material having a carrier mobility as high as possible is preferably used as the material for a semiconductor layer. The compounds represented by formulas (1) to (3) above, in particular, the compound of the formula (1) above has good film-formability when it is used as a material for the semiconductor layer, and thus applicable to a large-area field-effect transistor. In addition, the compound can be manufactured at low cost. Furthermore, for example, a pentacene derivative is decomposed in the air by moisture contained in the air. Likewise, the pentacene derivative is labile and difficult to handle. However, when the compounds represented by the formulas (1) to (3) above of the present invention is each used as a material for a semiconductor layer, they have advantages since the semiconductor layer manufactured is also highly stable and has a long life.

EXAMPLES

The present invention will be more specifically described by way of Examples; however, the present invention is not limited to these. In Examples, unless otherwise specified, the term "parts" represents "parts by mass" and "%" represents "% by mass", respectively.

The various types of compounds obtained in Synthesis Examples were, if needed, subjected to analysis for $^1$H-NMR, $^{13}$C-NMR(NMR: nuclear magnetic resonance spectrum), MS (mass spectrum), mp (melting point) and elemental analysis to determine structural formulas thereof. Measuring apparatuses are as follows:

NMR: JEOL Lambda 400 spectrometer
MS: Shimadzu QP-5050A
Elemental analysis: Parkin Elmer 2400 CHN type elemental analyzer

Synthesis Example 1

Synthesis of 2,7-Di(1-octynyl)[1]benzothieno[3,2-b][1]benzothiophene

[Formula 5]

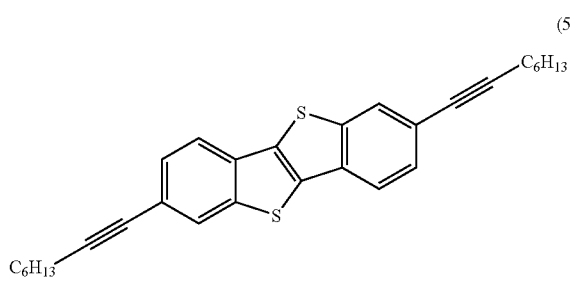

(5)

After 2,7-Diiodobenzothienobenzothiophene (1.0 g, 2.0 mmol) was dissolved in anhydrous diisopropylamine (15 ml) and anhydrous benzene (15 ml) under a nitrogen atmosphere, deaeration was performed for 30 minutes. To this, 10 mol % PdCl$_2$(PPh$_3$)$_2$ (140 mg), 20 mol % CuI (76 mg) and 1-octyn (0.81 ml, 5.5 mmol) were added and stirred at room temperature for 8 hours. After completion of stirring, water (30 ml) was added and extraction was performed with chloroform (30 ml×3). The extraction solution was washed with water (100 ml×3) and dried over anhydrous magnesium sulfate. The solvent was distilled away under reduced pressure and purification was performed by column chromatography (silica gel, methylene chloride: hexane=1:3, Rf=0.6). Recrystallization was performed from hexane to obtain the desired compound in the form of a colorless plate-crystal represented by the formula (5) above (yield: 710 mg, yield coefficient: 77%). This compound is the compound of Compound No. 88 of Table 1 above.

$^1$H-NMR (400 MHz, CDCl$_3$):
δ7.94 (s, 2H), 7.76 (d, J=8.2 Hz, 2H), 7.47 (d, J=8.2 Hz, 2H), 2.45 (t, J=7.1, 4H), 1.60-1.67 (m, 4H), 1.44-1.52 (m, 4H), 1.32-1.37 (m, 8H), 0.92 (t, J=6.8 Hz, 6H)

$^{13}$C-NMR (400 MHz, CDCl$_3$):
142.1, 134.0, 131.9, 128.4, 126.9, 121.1, 120.9, 91.5, 80.4, 31.4, 28.7, 22.6, 19.5, 14.1
MS (70ev, DI) m/z=456 (M$^+$)

mp 119-121° C.
Anal. Calcd for C$_{30}$H$_{32}$S$_2$: C, 78.90; H, 7.06.
Found: C, 79.03; H, 6.92.

Synthesis Example 2

Synthesis of 2,7-Dioctyl[1]benzothieno[3,2-b][1]benzothiophene

[Formula 6]

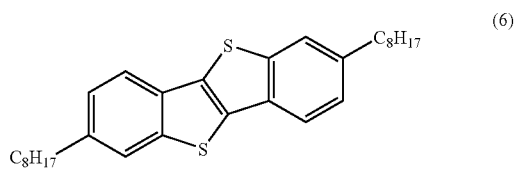

(6)

The compound (300 mg, 0.66 mmol) represented by the formula (5) above and obtained in Synthesis Example 1 and Pd/C (70 mg) were added to anhydrous toluene (10 mL). The reaction mixture was reduced in pressure by an aspirator and purged with hydrogen. This operation was repeated several times and then the reaction mixture was stirred for 8 hours. After completion of the reaction, the solvent was distilled away. Purification was performed by column chromatography (silica gel, hexane, Rf=0.6) (yield: 286 mg, yield coefficient: 94%) and recrystallization was performed from hexane to obtain the desired compound represented by the formula (6) above in the form of colorless powdery solid substance (yield: 250 mg, yield coefficient: 82%). This compound is the compound of Compound No. 16 of Table 1 above.

$^1$H-NMR (400 MHz, CDCl$_3$):
δ7.75 (d, J=8.2 Hz, 2H), 7.68 (d, J=1.5 Hz, 2H), 7.26 (dd, J=8.2, 1.5 Hz, 2H), 2.74 (t, J=7.7, 4H), 1.69 (q, 4H), 1.27-1.34 (m, 20H), 0.88 (t, J=6.7 Hz, 6H)

$^{13}$C-NMR (400 MHz, CDCl$_3$):
142.4, 140.0, 132.5, 131.1, 125.8, 123.3, 121.0, 36.1, 31.9, 31.7, 29.5, 29.33, 29.27, 22.68, 14.1
MS (70 ev, DI) m/z=464 (M$^+$)
mp 112-113° C.
Anal. Calcd for C$_{30}$H$_4$OS$_2$: C, 77.53; H, 8.67.
Found: C, 77.39; H, 8.67.

Synthesis Example 3

Synthesis of 2,7-Di(1-dodecynyl)[1]benzothieno[3,2-b][1]benzothiophene

[Formula 7]

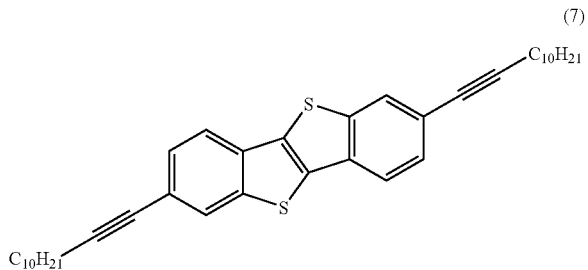

(7)

The same process as in Synthesis Example 1 was repeated except that 1-dodecyne was used in place of 1-octyne of Synthesis Example 1 to obtain the desired compound represented by the formula (7) above (yield: 966 mg, yield coefficient: 85%). This compound is the compound of Compound No. 91 of Table 1 above.

$^1$H-NMR (400 MHz, CDCl$_3$):
δ7.93 (dd, J=1.4, 0.52, 2H), 7.74 (dd, 7=0.52, 8.3 Hz, 2H), 7.45 (d, J=1.4, 8.3 Hz, 2H), 2.44 (t, J=7.1, 4H), 1.59-1.67 (m, 4H), 61.43-1.51 (m, 4H), 1.28-1.32 (m, 24H), 0.88 (t, J=6.8 Hz, 6H)

$^{13}$C-NMR (400 MHz, CDCl$_3$):
142.2, 134.0, 132.0, 128.4, 126.9, 121.2, 121.0, 91.6, 80.4, 31.9, 29.61, 29.56, 29.3, 29.2, 29.0, 28.8, 22.7, 19.5, 14.1

MS (70 ev, DI) m/z=568 (M$^+$)

mp 96-97° C.

Anal. Calcd for C$_{38}$H$_{48}$S$_2$: C, 80.22; H, 8.50.
Found: C, 80.12; H, 8.34.

Synthesis Example 4

Synthesis of 2,7-Didodecyl[1]benzothieno[3,2-b][1]benzothiophene

[Formula 8]

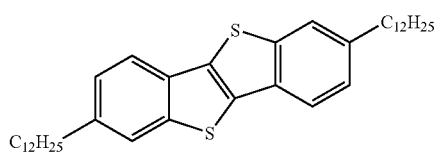

(8)

The same process as in Synthesis Example 2 was repeated except that the compound of the formula (7) above was used in place of the compound of the formula (5) above to obtain the desired compound represented by the formula (8) above (yield: 375 mg, yield coefficient: 88%). The compound is the compound of Compound No. 20 of Table 1 above.

$^1$H-NMR (400 MHz, CDCl$_3$):
δ7.77 (d, J=8.3 Hz, 2H), 7.70 (d, J=1.2, 2H), 7.27 (dd, J=1.2, 8.3 Hz, 2H), 2.75 (t, J=7.8, 4H), 1.65-1.72 (m, 4H), 1.25-1.34 (m, 36H), 0.87 (t, J=6.8 Hz, 6H)

$^{13}$C-NMR (400 MHz, CDCl$_3$):
142.4, 140.0, 132.5, 131.1, 125.8, 123.3, 121.0, 36.1, 31.9, 31.7, 29.65, 29.63, 29.58, 29.51, 29.35, 29.29, 22.7, 14.1

MS (70 ev, DI) m/z=576 (M$^+$)

mp 114-115° C.

Anal. Calcd for C$_{38}$H$_{56}$S$_2$: C, 79.10; H, 9.78.
Found: C, 79.19; H, 9.85.

Synthesis Example 5

Synthesis of 2,7-bi(1-dodecynyl)[1]benzoselenopheno[2,3-b]benzoselenophene

[Formula 9]

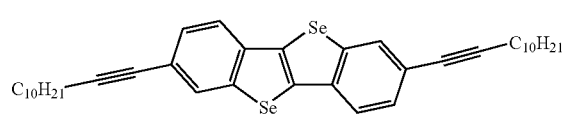

(9)

The same process as in Synthesis Example 1 was repeated except that a reaction was performed using 2,7-dibromobenzoselenobenzoselenophene (296 mg, 0.5 mmol) in place of 2,7-diiodobenzothienobenzothiophene (1.0 g, 2.0 mmol) and using anhydrous toluene in place of anhydrous benzene, under reflux to obtain the desired compound represented by the formula (9) above (yield: 187 mg, yield coefficient: 56%). This compound is the compound of Compound No. 97 of Table 1 above.

$^1$H-NMR (400 MHz, CDCl$_3$):
δ7.97 (s, 2H), 7.68 (d, J=8.0 Hz, 2H), 7.45 (d, J=8.0 Hz, 2H), 2.44 (t, J=6.8 Hz, 4H), 1.60-1.67 (m, 4H), 1.42-1.50 (m, 24H), 1.20-1.39 (m, 24H), 0.87 (t, J=6.4 Hz, 6H)

MS (EI) m/z=664 (M$^+$)

mp 73-74° C.

Synthesis Example 6

Synthesis of 2,7-Didodecyl-[1]benzoselenopheno[2,3-b]benzoselenophene

[Formula 10]

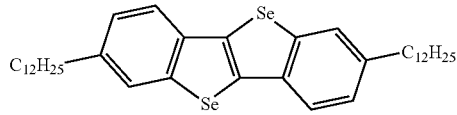

(10)

The same process as in Synthesis Example 2 was repeated except that the compound of the formula (9) above was used in place of the compound of the formula (5) above to obtain the desired compound represented by the formula (10) above (yield: 229 mg, yield coefficient: 82%). This compound is the compound of Compound No. 51 of Table 1 above.

$^1$H-NMR (400 MHz, CDCl$_3$):
δ7.75 (s, 2H), 7.68 (d, J=8.0 Hz, 2H), 7.25 (d, J=8.0 Hz, 2H), 2.72 (t, J=7.6 Hz, 4H), 1.60-1.70 (m, 4H), 1.18-1.33 (m, 36H), 0.88 (t, J=6.8 Hz, 6H)

MS (EI) m/z=672 (M$^+$)

mp 110-111° C.

Example 1

The compound of Compound No. 16 obtained in Synthesis Example 2 was dissolved in chloroform so as to obtain a concentration of 0.4% to prepare ink for manufacturing a semiconductor device.

The ink thus obtained was applied onto an n-doped silicon wafer (surface resistance: 0.02 Ω·cm or less) provided with a SiO$_2$ thermal oxidation film of 200 nm in accordance with a spin coating method (4000 rpm, 25 seconds) to form a semiconductor thin film (layer), which was further subjected to a heat treatment performed under argon at 80° C. for 30 minutes.

Subsequently, the substrate was placed in a vacuum deposition apparatus, which was then evacuated until the degree of vacuum of the apparatus became $1.0 \times 10^{-3}$ Pa or less. Gold electrodes (source and drain electrodes) of 40 nm in thickness were formed by deposition in accordance with a resistance-heating deposition method to obtain a field-effect transistor of the present invention. In the field-effect transistor of this example, the thermal oxidation film provided to the n-doped silicon wafer serves as the insulating layer (4) and the n-doped silicon wafer serves as the substrate (6) and the gate layer (5) (see FIG. 3).

The field-effect transistor thus obtained was placed in a prober and semiconductor characteristics were measured by a semiconductor parameter analyzer under the atmosphere. As the semiconductor characteristics, gate voltage was scanned every 20 V from 10 V to −100 V and drain voltage was scanned from 10 V to −100 V to measure a drain current-a drain voltage. As a result, current saturation was observed. Based on the voltage current curve obtained, it was found that the device of this example was a p-type semiconductor having a carrier mobility of 0.66 cm$^2$/Vs, an ON/OFF ratio of 1×10$^7$ and a threshold of −47 V.

Example 2

The same process as in Example 1 was repeated except that the compound of Compound No. 16 of Example 1 was replaced by the compound of Compound No. 20 obtained in Synthesis Example 4 above to obtain an organic field-effect transistor of the present invention. The semiconductor characteristics thereof were measured in the same manner. As a result, it was found that the device of this example is a p-type semiconductor having a carrier mobility of 0.61 cm$^2$/Vs, an ON/OFF ratio of 1×10$^7$ and a threshold of −25 V.

Example 3

The same process as in Example 1 was repeated except that the compound of Compound No. 16 of Example 1 was replaced by the compound of Compound No. 88 obtained in Synthesis Example 1 above to obtain an organic field-effect transistor of the present invention. The semiconductor characteristics thereof were measured in the same manner. As a result, it was found that the device of this example is a p-type semiconductor having a carrier mobility of 4×10$^{-5}$ cm$^2$/Vs, an ON/OFF ratio of 1×10$^2$ and a threshold of −35V.

Example 4

The same process as in Example 1 was repeated except that the compound of Compound No. 16 was replaced by the compound of Compound No. 51 obtained in Synthesis Example 6 above to obtain an organic field-effect transistor of the present invention. The semiconductor characteristics thereof were measured in the same manner. As a result, it was found that the device of this example is a p-type semiconductor having a carrier mobility of 0.012 cm$^2$/Vs, an ON/OFF ratio of 1×10$^4$ and a threshold of −30 V.

Example 5

The compound of Compound No. 16 obtained in Synthesis Example 2 above was dissolved in chloroform so as to obtain a concentration of 0.4% to prepare ink for manufacturing a semiconductor device.

The ink thus obtained was applied onto an n-doped silicon wafer (surface resistance: 0.02 Ω·cm or less) provided with a SiO$_2$ thermal oxidation film of 200 nm in accordance with a spin coating method (4000 rpm, 25 seconds) to form a semiconductor thin film (layer).

Subsequently, the substrate was placed in a vacuum deposition apparatus, which was then evacuated until the degree of vacuum of the apparatus became 1.0×10$^{-3}$ Pa or less. Gold electrodes (source and drain electrodes) of 40 nm in thickness were formed by a resistance-heating deposition method and then subjected to a heat treatment performed under nitrogen at 80° C. for 30 minutes to obtain a field-effect transistor according to the present invention.

The field-effect transistor thus obtained was placed in a prober and semiconductor characteristics were measured by a semiconductor parameter analyzer under the atmosphere. As the semiconductor characteristics, gate voltage was scanned every 20 V from 10 V to −100V and drain voltage was scanned from 10 V to −100 V to measure a drain current-a drain voltage. As a result, current saturation was observed. Based on the voltage current curve obtained, it was found that the device of this example was a p-type semiconductor having a carrier mobility of 0.9 cm$^2$/Vs, an ON/OFF ratio of 1×10$^7$ and a threshold of −47 V.

Example 6

The same process as in Example 1 was repeated except that the compound of Compound No. 16 of Example 5 was replaced by the compound of Compound No. 20 obtained in Synthesis Example 4 above to obtain an organic field-effect transistor of the present invention. The semiconductor characteristics thereof were measured in the same manner. As a result, it was found that the device of this example is a p-type semiconductor having a carrier mobility of 1.2 cm$^2$/Vs, an ON/OFF ratio of 1×10$^7$ and a threshold of −25 V.

Example 7

A resist material was applied onto an n-doped silicon wafer (surface resistance: 0.02 Ω·cm or less) provided with a SiO$_2$ thermal oxidation film of 300 nm treated with hexamethyldisilazane, exposed to light to make a pattern, on which chromium was deposited in a thickness of 1 nm and further gold was deposited in a thickness of 40 nm. Subsequently, the resist was removed to form a source electrode (1) and a drain electrode (3) (a comb-type electrode: a channel length of 25 μm×a channel width of 2 mm×20).

The compound of Compound No. 16 obtained in Synthesis Example 2 above was dissolved in toluene so as to obtain a concentration of 1% to prepare ink for manufacturing a semiconductor device.

The comb-type electrode was dipped in the ink for manufacturing a semiconductor device and directly pulled up at a speed of 5 mm/sec. Dip-coating was thus performed to form a semiconductor layer (film). The resultant thin film was subjected to a heat treatment performed under the atmosphere at 80° C. for 5 minutes to obtain a bottom-contact type field-effect transistor of the present invention. In the field-effect transistor of this example, the thermal oxidation film provided to the n-doped silicon wafer serves as the insulating layer (4) and the n-doped silicon wafer serves as the substrate (6) and the gate layer (5) (see FIG. 1-A).

The field-effect transistor thus obtained was placed in a prober and semiconductor characteristics were measured by a semiconductor parameter analyzer under the atmosphere. As the semiconductor characteristics, gate voltage was scanned every 20 V from 10 V to −100 V and drain voltage was scanned from 10 V to −100 V to measure a drain current-a drain voltage. As a result, current saturation was observed. Based on the voltage current curve obtained, it was found that the device of this example is a p-type semiconductor having a carrier mobility of 0.59 cm$^2$/Vs, an ON/OFF ratio of 1×10$^7$ and a threshold of −52 V.

Example 8

The compound of Compound No. 16 obtained in Synthesis Example 2 above was dissolved in toluene so as to obtain a concentration of 1% to prepare ink for manufacturing a semiconductor device.

The ink thus obtained was applied onto an n-doped silicon wafer (surface resistance: 0.02 Ω·cm or less) provided with a SiO$_2$ thermal oxidation film of 300 nm by a printer system (machine name: Apollo II manufactured by Spectra) having a piezo head. An inkjet recording method was thus performed to obtain a coated and patterned semiconductor thin film (layer). The resultant thin film was further subjected to a heat treatment performed under the atmosphere at 80° C. for 5 minutes under the atmosphere.

Subsequently, the substrate was placed in a vacuum deposition apparatus, which was then evacuated until the degree of vacuum of the apparatus became 1.0×10$^{-3}$ Pa or less. Gold electrodes (source and drain electrodes) of 40 nm in thickness were formed by deposition in accordance with a resistance-heating deposition method to obtain a top-contact type field-effect transistor of the present invention. In the field-effect transistor of this example, the thermal oxidation film provided to the n-doped silicon wafer serves as the insulating layer (4) and the n-doped silicon wafer serves as the substrate (6) and the gate layer (5) (see FIG. 1-B).

The field-effect transistor thus obtained was placed in a prober and semiconductor characteristics were measured by a semiconductor parameter analyzer under the atmosphere. As the semiconductor characteristics, gate voltage was scanned every 20 V from 10 V to −100 V and drain voltage was scanned from 10 V to −100 V to measure a drain current-a drain voltage. As a result, current saturation was observed. Based on the voltage current curve obtained, it was found that the device of this example is a p-type semiconductor having a carrier mobility of 0.086 cm$^2$/Vs, an ON/OFF ratio of 1×10$^4$ and a threshold of −50 V.

Example 9

The compound of Compound No. 16 obtained in Synthesis Example 2 above was dissolved in toluene so as to obtain a concentration of 1% to prepare ink for manufacturing a semiconductor device.

Using the ink thus obtained, coat-patterning was performed by a printer system (machine name: Apollo II manufactured by Spectra) having a piezo head in accordance with an inkjet recording method on the same comb type electrode as in Example 7 to form a semiconductor thins film (layer). The resultant thin film was subjected to a heat treatment performed under the atmosphere at 80° C. for 5 minutes to obtain a bottom-contact type field-effect transistor of the present invention. In the field-effect transistor of this example, the thermal oxidation film provided to the n-doped silicon wafer serves as the insulating layer (4) and the n-doped silicon wafer serves as the substrate (6) and the gate layer (5) (see FIG. 1-A).

The field-effect transistor thus obtained was placed in a prober and semiconductor characteristics were measured by a semiconductor parameter analyzer under the atmosphere. As the semiconductor characteristics, gate voltage was scanned every 20 V from 10 V to −100 V and drain voltage was scanned from 10 V to −100 V to measure a drain current-a drain voltage. As a result, current saturation was observed. Based on the voltage current curve obtained, it was found that the device of this example is a p-type semiconductor having a carrier mobility of 0.085 cm$^2$/Vs, an ON/OFF ratio of 1×10$^6$ and a threshold of −56 V.

Example 10

The compound of Compound No. 16 obtained in Synthesis Example 2 above was dissolved in tetrahydrofuran so as to obtain a concentration of 1% to prepare ink for manufacturing a semiconductor device.

The ink thus obtained was applied onto an n-doped silicon wafer (surface resistance: 0.02 Ω·cm or less) provided with a SiO$_2$ thermal oxidation film of 300 nm in accordance with a spin coating method (2000 rpm, 20 seconds) to form a semiconductor thin film, which was further subjected to heat treatment performed under the atmosphere at 80° C. for 10 minutes.

Subsequently, the substrate was placed in a vacuum deposition apparatus, which was then evacuated until the degree of vacuum of the apparatus became 1.0×10$^{-3}$ Pa or less. Gold electrodes (source and drain electrodes) of 40 nm in thickness were formed by deposition in accordance with a resistance-heating deposition method to obtain a top-contact type field-effect transistor of the present invention. In the field-effect transistor of this example, the thermal oxidation film provided to the n-doped silicon wafer serves as the insulating layer (4) and the n-doped silicon wafer serves as the substrate (6) and the gate layer (5) (see FIG. 1-B).

The field-effect transistor thus obtained was placed in a prober and semiconductor characteristics were measured by a semiconductor parameter analyzer under the atmosphere. As the semiconductor characteristics, gate voltage was scanned every 20 V from 10 V to −100 V and drain voltage was scanned from 10 V to −100 V to measure a drain current-a drain voltage. As a result, current saturation was observed. Based on the voltage current curve obtained, it was found that the device of this example is a p-type semiconductor having a carrier mobility of 2.5 cm$^2$/Vs, an ON/OFF ratio of 1×10$^8$ and a threshold of −58 V.

Example 11

The compound of Compound No. 16 obtained in Synthesis Example 2 above was dissolved in cyclopentanone so as to obtain a concentration of 0.5% to prepare ink for manufacturing a semiconductor device.

The ink thus obtained was applied onto an n-doped silicon wafer (surface resistance: 0.02 Ω·cm or less) provided with a SiO$_2$ thermal oxidation film of 300 nm in accordance with a spin coating method (2000 rpm, 20 seconds) to form a semiconductor thin film (layer), which was further subjected to heat treatment performed under the atmosphere at 80° C. for 10 minutes.

Subsequently, the substrate was placed in a vacuum deposition apparatus, which was then evacuated until the degree of vacuum of the apparatus became 1.0×10$^{-3}$ Pa or less. Gold electrodes (source and drain electrodes) of 40 nm in thickness were formed by deposition in accordance with a resistance-heating deposition method to obtain a top-contact type field-effect transistor of the present invention. In the field-effect transistor of this example, the thermal oxidation film provided to the n-doped silicon wafer serves as the insulating layer (4) and the n-doped silicon wafer serves as the substrate (6) and the gate layer (5) (see FIG. 1-B).

The field-effect transistor thus obtained was placed in a prober and semiconductor characteristics were measured by a semiconductor parameter analyzer under the atmosphere. As the semiconductor characteristics, gate voltage was scanned every 20 V from 10 V to −100 V and drain voltage was scanned from 10 V to −100 V to measure a drain current-a drain voltage. As a result, current saturation was observed. Based on the voltage current curve obtained, it was found that the device of this example is a p-type semiconductor having a carrier mobility of 4.5 cm$^2$/Vs, an ON/OFF ratio of 1×10$^8$ and a threshold of −64 V.

Solubility Test 1

To confirm solubility to solvent, which is one of the important characteristics of a semiconductor manufactured by coating, the solubility of a test compound to toluene was measured. A test compound was added to toluene little by little at room temperature and stirred. The solubility was determined by visually checking whether it was dissolved or not. When the test compound remained undissolved, the total amount by mass of the test compound added immediately before the moment was calculated and the solubility to toluene was expressed in terms of % by mass. The results are shown in Table 2.

The "Compound No." of Table 2 is the same as defined in Table 1. Furthermore, in Comparative Example 1, the solubility of Compound 16 of Example 15 disclosed in Patent Document 3 to toluene was calculated by the same test method as above. The structural formula of the compound used in Comparative Example 1 is shown in the formula (101) below.

[Formula 11]

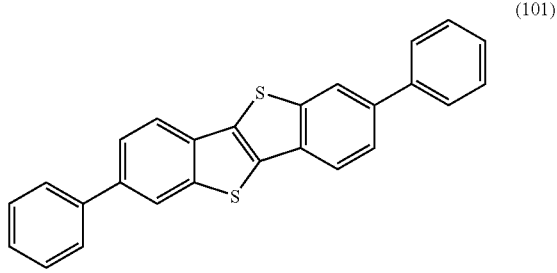

(101)

TABLE 2

| Results of solubility test | |
| --- | --- |
| Compound No. | Solubility (% by mass) |
| 16 | 1.5 |
| 20 | 0.2 |
| Comparative Example 1 | 0.01 or less |

As is apparent from the results of Table 2, the compounds Nos. 16 and 20 used in Examples 1, 7 to 11 and Example 2 exhibit solubility to toluene, which is at least 50 fold and 20 fold as large as that of the aryl derivative used in Comparative Example 1. It is found that the compounds have sufficiently suitable properties for printing.

Solubility Test 2

To confirm solubility to solvent, the solubility of a test compound to chloroform was measured. A test compound was added to chloroform little by little at room temperature and stirred. The solubility was determined by visually checking whether it was dissolved or not. When the test compound remained undissolved, the total amount by mass of the test compound added immediately before the moment was calculated and the solubility to chloroform was expressed in terms of % by mass. The results are shown in Table 3.

The "Compound No." of Table 3 is the same as defined in Table 1.

TABLE 3

| Results of solubility test | |
| --- | --- |
| Compound No. | Solubility (% by mass) |
| 8 | 4.1 |
| 12 | 4.7 |
| 14 | 4.7 |
| 16 | 5.4 |
| 17 | 6.1 |
| 18 | 1.6 |
| 20 | 0.6 |
| 22 | 0.2 |

As is apparent from the results of Table 3, the compounds of the present invention including the compounds of Compound Nos. 16 and 20 used in Examples 1, 7 to 11 and Example 2 exhibit sufficient solubility also to chloroform. It is found that the compounds have sufficiently suitable properties for printing.

Based on the semiconductor properties described in each Example and the solubility test results shown in Tables 2 and 3, it was confirmed that the field-effect transistor of the present invention can be operated stably in the atmosphere as well as has high semiconductor characteristics. It was also confirmed that the semiconductor layer can be simply manufactured at low cost by e.g. a coating method without using a vacuum deposition method requiring specific equipment.

Furthermore, based on comparison between Examples 1 and 5 and Examples 2 and 6, it was found that the heat treatment during the manufacturing process for a transistor according to the present is more preferably performed in view of carrier mobility after a semiconductor film was formed and further electrodes are formed by deposition.

In conventional organic field-effect transistors using a pentacene derivative, etc., the compound used in the semiconductor layer is known to be decomposed by humidity contained in the atmosphere and thus the stability in the atmosphere is a problem. However, the transistor of the present invention manufactured in each Example was found to have sufficient stability in the atmosphere since the values of semiconductor characteristics that were again measured 10 days later are the same as the initially measured ones. Accordingly, the field-effect transistor of the present invention is extremely useful.

Examples 12 to 22

Test for Heat Treatment Effect of Semiconductor Layer

Compound No. 16 shown in Table 1 and obtained in Synthesis Example 2 above was dissolved in chloroform to prepare ink containing 1.0 wt % of the compound for manufacturing a semiconductor device of the present invention. The obtained ink (about 10 μL) was put dropwise to an n-doped silicon wafer (surface resistance: 0.02 Ω·cm or less) provided with a $SiO_2$ thermal oxidation film of 200 nm and subjected to spin coating performed at 3000 to 4500 rpm for 20 to 30 seconds to form a semiconductor thin film in the same manner as in Example 1.

To observe the effects of different heat treatment conditions upon the transistor performance, the n-doped silicon wafers having a semiconductor thin film formed thereon and gold electrodes formed by deposition thereon were subjected to different heat treatments and thereafter charge mobility values of the field-effect transistors of the present invention were separately measured. Note that the semiconductor thin film contained in the transistor of the present invention is sufficiently stable even under the atmosphere. Therefore, the heat treatment was performed by placing the n-doped silicon wafer on a hot plate for 10 minutes in the atmosphere. The results are shown in Table 4. The melting point of Compound No. 16 used in this test was 129 to 131° C. and had two thermal phase transition points of 109° C. and 128° C. when measured while raising the temperature and two thermal phase transition points of 127° C. and 99° C. when measured while decreasing the temperature.

The heat treatment was performed at the following five temperatures with reference to the above measured values of thermal phase transition point:
1) Heat treatment is not performed
2) Heat treatment is performed at 80° C., which is lower than the lower limit of the thermal phase transition point
3) Heat treatment is performed at 100° C., which almost corresponds to the lower limit of the thermal phase transition point
4) Heat treatment is performed at 120° C. within the range of the thermal phase transition point
5) Heat treatment is performed at 130° C. which is more than the melting initiation temperature.

Reference Examples 1 and 2

Field-effect transistors of Reference Examples 1 and 2 were obtained in the same manner as Examples 16 and 14 except that the heat treatment temperature was set at 130° C. The charge mobility values of the transistors were measured and the results are shown in Table 4 below.

TABLE 4

| | Heat treatment temperature (° C.) | | |
| --- | --- | --- | --- |
| | After formation of semiconductor film | After formation of electrodes by deposition | Charge mobility (cm$^2$/Vs) |
| Example 12 | 120 | 100 | 1.3-1.8 |
| Example 13 | 120 | 80 | 0.9-1.8 |
| Example 14 | 120 | Not treated | 0.7-1.3 |
| Example 15 | 80 | 120 | 0.6-0.8 |
| Example 16 | Not treated | 120 | 0.5-0.8 |
| Example 17 | 80 | 80 | 0.19-0.24 |
| Example 18 | Not treated | 100 | 0.09-0.23 |
| Example 19 | Not treated | 80 | 0.14-0.2 |
| Example 20 | 80 | Not treated | 0.12-0.2 |
| Example 21 | 80 | 100 | 0.16-0.19 |
| Example 22 | Not treated | Not treated | 0.08-0.17 |
| Reference Example 1 | Not treated | 130 | Not detected |
| Reference Example 2 | 130 | Not treated | Not detected |

As is apparent from Table 4, the charge mobility of Example 22 in which no heat treatment was performed is 0.08 to 0.17 cm$^2$/Vs, whereas the charge mobility of Examples 17 to 21 in which the heat treatment was performed at 80° C. or 100° C. or less ranges 0.09 to 0.24 cm$^2$/Vs. It was observed that charge mobility tends to increase in the samples to which the heat treatment was applied. Furthermore, the charge mobility of Examples 12 to 16, in which the heat treatment was performed at 120° C. in either process, is as extremely high as 0.5 to 1.8 cm$^2$/Vs. From this, it was elucidated that the heat treatment is more preferably performed at an appropriate temperature.

On the other hand, the charge mobility of Examples 17 to 22 in which the heat treatment is performed at 100° C. or less are lower than that of Examples 12 to 16 in which the heat treatment is performed at 120° C.

Furthermore, in References Examples 1 and 2 in which a heat treatment was performed at 130° C., field-effect transistor characteristics were not observed.

According to the differential thermal analysis (DSC) of the compounds used in the aforementioned test for heat treatment effect of the semiconductor layer, two decalescent points were observed at 109° C. and 128° C. during a temperature-raising process and two exothermic points were observed at 127° C. and 99° C. during a temperature-decreasing process. The same thermal points were obtained even if the same sample was repeatedly measured. The results show that the compound has two phase transition temperatures. The phase transition at the lower temperature side seems to be the transition from a solid state to a liquid crystal state; whereas the phase transition at the higher temperature side seems to be the transition from the liquid crystal state to a molten state or a melting state. When the material is treated with heat at 120° C., the state of the material changes to the state of a liquid crystal in which the molecular arrangement may possibly occur. Since the molecules are arranged suitable for charge migration, charge mobility may conceivably be improved. On the other hand, in Reference Examples 1 and 2 in which heat treatment was applied at more than the melting initiation temperature of 130° C., it was visually observed that a thin film flows down from the substrate as the compound melts. For the reason, it is considered that no transistor characteristics were observed.

Also from these results, it is desirable that the heat treatment temperature is appropriately selected.

Comparative Example 2

In Comparative example 2, the semiconductor characteristics of the compound represented by the formula (101) above were examined.

The solubility of the compound represented by the formula (101) to toluene is not more than 0.01% by mass as mentioned above. Even if this solution is used, no coating film is formed, meaning that the compound has no properties suitable for printing. Therefore, the compound was not able to be used as a semiconductor material for a coating-type field-effect transistor. Therefore, using chloroform, to which the compound shows a solubility of 0.02% by mass, which is high than that of toluene, as an organic solvent, a semiconductor was manufactured as follows.

After a chloroform suspension solution of the compound represented by the formula (101) above was prepared, insoluble solid substances were filtered off to obtain a filtrate. The solubility of the compound represented by the formula (101) above to the filtrate was 0.02% by mass.

The same operation as in Example 1 was repeated except that the filtrate thus obtained was used as ink for manufacturing a semiconductor derive, to obtain a field-effect transistor for use in comparison. In the obtained transistor, formation of a semiconductor layer was not visually observed. To confirm this, the semiconductor characteristics were measured in the same manner as in Example 1. However, there was no current flow when the obtained transistor was used. The compound had no nature as a semiconductor.

As is apparent from Comparative Example 2 above, the compound represented by the formula (101) above has extremely low solubility to an organic solvent. Therefore, it is extremely difficult to manufacture a transistor by coating. In contrast, the compound represented by the formula (1) above to be used in the transistor of the present invention has sufficiently high solubility to an organic solvent and is thus said to be extremely suitable for use as a semiconductor material for a coating type field-effect transistor.

INDUSTRIAL APPLICABILITY

According to the present invention, use of a compound having a specific structure and a high solubility to an organic solvent makes it possible to provide a field-effect transistor that can be manufactured by a method such as coating or printing and shows excellent carrier mobility.

DESCRIPTION OF REFERENCE NUMERALS

Figure 1:
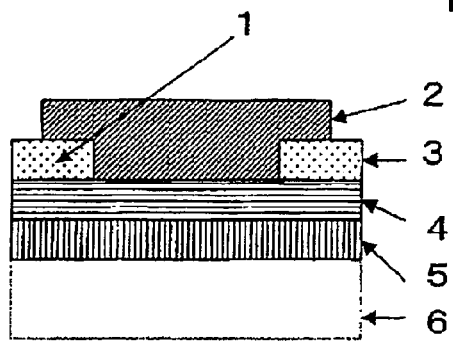
FIG. 1 shows schematic views of the structural embodiments of field-effect transistors of the present invention.
Figure 1:
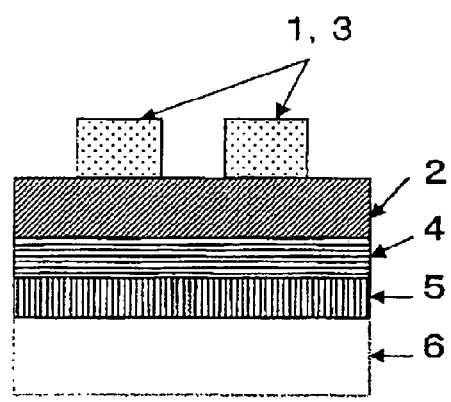
Figure 1:
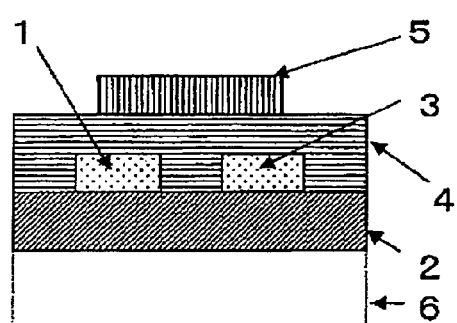
Figure 1:
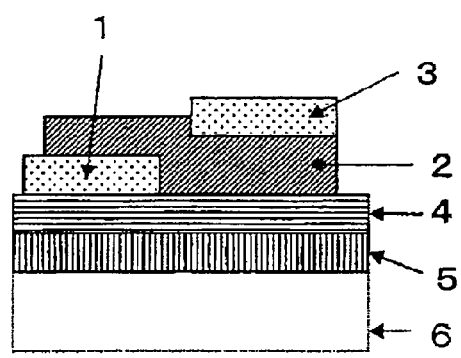
Figure 1:
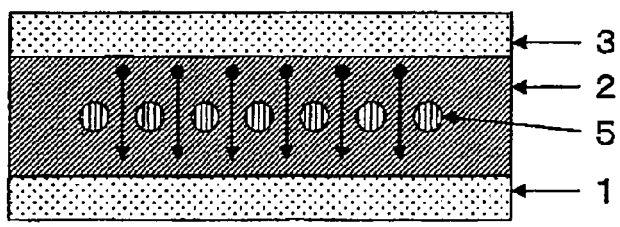
Figure 2:
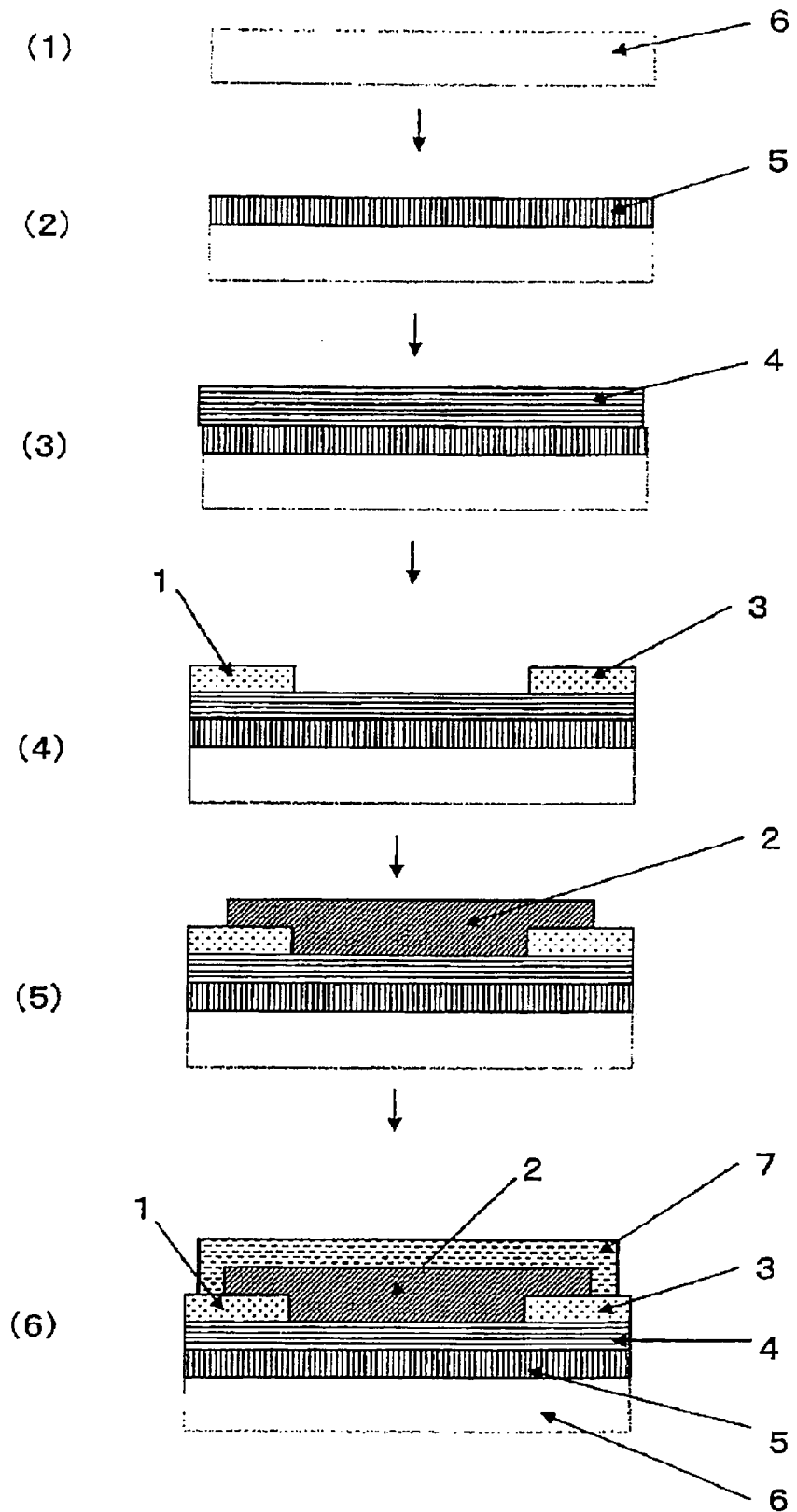
FIG. 2 shows schematic views illustrating the steps of manufacturing an embodiment of a field-effect transistor of the preset invention.
Figure 3:
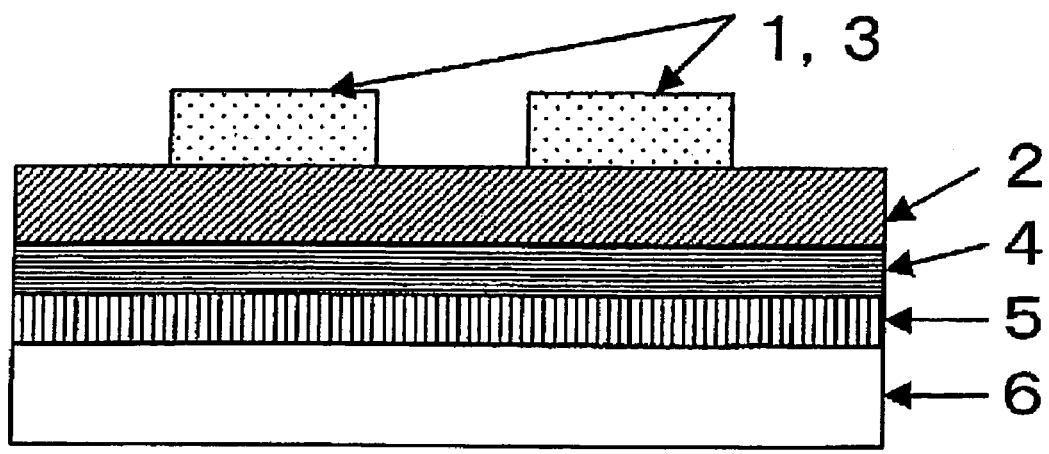
FIG. 3 shows a schematic view of the field-effect transistor of the present invention obtained in Example 1.

Like reference numerals designate like structural elements in FIGS. 1 to 3.
1. Source electrode
2. Semiconductor layer
3. Drain electrode
4. Insulating layer
5. Gate electrode
6. Substrate
7. Protective layer

The invention claimed is:

1. A field-effect transistor characterized by containing a compound represented by formula (1) below as a semiconductor material:

[Formula 1]

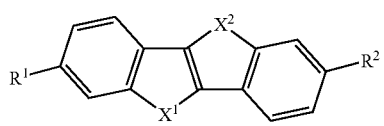

(1)

(wherein, $X^1$ and $X^2$ are each independently a sulfur atom, a selenium atom or a tellurium atom; and $R^1$ and $R^2$ are each independently an unsubstituted or halogeno-substituted C1 to C36 aliphatic hydrocarbon group).

2. The field-effect transistor according to claim 1, wherein $X^1$ and $X^2$ in the formula (1) are each independently a sulfur atom or a selenium atom.

3. The field-effect transistor according to claim 1, wherein $X^1$ and $X^2$ in the formula (1) are each a sulfur atom.

4. The field-effect transistor according to claim 1, wherein $R^1$ and $R^2$ in the formula (1) are each independently an unsubstituted or halogeno-substituted C2 to C24 aliphatic hydrocarbon group.

5. The field-effect transistor according to claim 1, wherein $R^1$ and $R^2$ in the formula (1) are each independently an unsubstituted or halogeno-substituted C4 to C20 aliphatic hydrocarbon group.

6. The field-effect transistor according to claim 1, wherein $R^1$ and $R^2$ in the formula (1) are each independently an unsubstituted aliphatic hydrocarbon group.

7. The field-effect transistor according to claim 6, wherein $R^1$ and $R^2$ in the formula (1) are each independently a saturated aliphatic hydrocarbon group.

8. The field-effect transistor according to claim 7, wherein $R^1$ and $R^2$ in the formula (1) are each independently a straight-chain aliphatic hydrocarbon group.

9. The field-effect transistor according to claim 1, having a top-contact type structure, characterized in that the layer containing a compound represented by the formula (1) is provided on an insulating layer provided on a gate electrode, and further a source electrode and a drain electrode are separately provided so as to be in contact with an upper portion of the layer.

10. The field-effect transistor according to claim 1, characterized in that the layer containing a compound represented by the formula (1) is provided on electrodes of a bottom-contact type structure, which has an insulating layer, a gate electrode isolated by the insulating layer, and a source electrode and a drain electrode provided so as to be in contact with the insulating layer.

11. The field-effect transistor according to claim 9, characterized in that the layer containing a compound represented by the formula (1) is provided by an inkjet recording method.

12. Ink for manufacturing a semiconductor device characterized by containing a compound represented by the formula (1).

13. A method for manufacturing a field-effect transistor characterized by forming a semiconductor layer by applying the ink for manufacturing a semiconductor device according to claim 12 onto a substrate and drying the ink.

14. The method for manufacturing a field-effect transistor according to 13, characterized in that the application of ink is performed by an inkjet recording method.

15. The method for manufacturing a field-effect transistor according to claim 13, characterized by forming the semiconductor layer in the atmosphere.

16. The method for manufacturing a field-effect transistor according to claim 13, characterized by performing a heat treatment after the semiconductor layer is formed.

17. The method for manufacturing a field-effect transistor according to claim 16, characterized in that temperature of the heat treatment is 40 to 120° C.

18. A compound represented by formula (2) below:

[Formula 2]

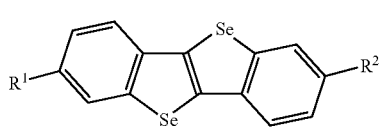

(2)

(wherein $R^1$ and $R^2$ are each independently an unsubstituted or halogeno-substituted C1 to C36 aliphatic hydrocarbon group).

19. A compound represented by formula (3) below:

[Formula 3]

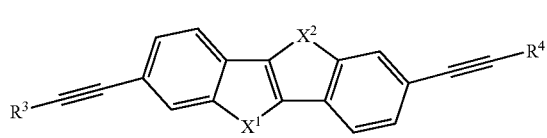
(3)

(wherein, $R^3$ and $R^4$ are each independently an unsubstituted or halogeno-substituted C1 to C34 aliphatic hydrocarbon group; and $X^1$ and $X^2$ are each independently a sulfur atom, a selenium atom or a tellurium atom).

20. The field-effect transistor according to claim 1, wherein $R^1$ and $R^2$ in the formula (1) are each independently an unsaturated aliphatic hydrocarbon group.

21. The field-effect transistor according to claim 1, wherein $R^1$ and $R^2$ in the formula (1) are each independently a branched aliphatic hydrocarbon group.

22. The compound according to claim 18, wherein $R^1$ and $R^2$ in the formula (2) are each independently an unsaturated or branched aliphatic hydrocarbon group.

23. The compound according to claim 19, wherein $R^3$ and $R^4$ in the formula (3) are each independently an unsaturated or branched aliphatic hydrocarbon group.

24. A field-effect transistor according to claim 1, wherein $R^1$ and $R^2$ are each independently an unsubstituted C1 to C36 aliphatic hydrocarbon group.

25. A field-effect transistor according to claim 1, wherein $R^1$ and $R^2$ are each independently an unsubstituted C4 to C20 aliphatic hydrocarbon group.

26. A field-effect transistor according to claim 1, wherein $R^1$ and $R^2$ are each independently an unsubstituted C4 to C14 aliphatic hydrocarbon group.

27. A field-effect transistor according to claim 1, wherein $R^1$ and $R^2$ are each an n-C8H17 group.

28. A field-effect transistor according to claim 1, wherein $R^1$ and $R^2$ are each an n-C12H25 group.

* * * * *